United States Patent
Panigrahi et al.

(10) Patent No.: US 6,851,662 B2
(45) Date of Patent: Feb. 8, 2005

(54) ON-THE-GO SUGAR SENSOR FOR DETERMINING SUGAR CONTENT DURING HARVESTING

(75) Inventors: Suranjan Panigrahi, Fargo, ND (US); Vernon Hofman, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 0 days.

(21) Appl. No.: 10/632,048

(22) Filed: Jul. 31, 2003

(65) Prior Publication Data

US 2004/0021862 A1 Feb. 5, 2004

Related U.S. Application Data

(62) Division of application No. 09/758,392, filed on Jan. 12, 2001, now Pat. No. 6,624,888.
(60) Provisional application No. 60/175,636, filed on Jan. 12, 2000.

(51) Int. Cl.[7] .................................................. G01J 3/28
(52) U.S. Cl. ..................................................... 256/326
(58) Field of Search ......................... 356/326, 32, 328, 356/73.1, 69

(56) References Cited

U.S. PATENT DOCUMENTS

| | | | |
|---|---|---|---|
| 3,578,866 A | 5/1971 | Kohler et al. .................. 356/74 |
| 3,597,616 A | 8/1971 | Brunton et al. ............. 250/83.3 |
| 3,776,642 A | 12/1973 | Anson et al. ................ 356/188 |
| 3,861,788 A | 1/1975 | Webster ...................... 350/315 |
| 3,876,881 A | 4/1975 | Bohlen .................... 250/361 C |
| 3,886,331 A | 5/1975 | Schierer ...................... 356/308 |
| 4,037,970 A | 7/1977 | Webster et al. ............. 356/188 |
| 4,040,747 A | 8/1977 | Webster ....................... 356/188 |
| 4,108,847 A | 8/1978 | Creinin et al. .......... 260/112 G |
| 4,146,332 A | 3/1979 | Moore ........................ 356/308 |
| 4,253,766 A | 3/1981 | Funk .......................... 356/418 |
| 4,260,262 A | 4/1981 | Webster ....................... 326/418 |
| 4,448,790 A | 5/1984 | Sarkki et al. .................. 426/52 |
| 4,463,261 A | 7/1984 | Bowman ...................... 250/339 |
| 4,540,282 A | 9/1985 | Landa et al. ................. 356/328 |
| 4,560,275 A | 12/1985 | Goetz .......................... 356/326 |
| 4,649,281 A | 3/1987 | Schmitt et al. ............. 250/574 |
| 4,806,764 A | 2/1989 | Satake ......................... 250/339 |
| 4,836,017 A | 6/1989 | Bozek ..................... 73/152.42 |
| 4,866,644 A | 9/1989 | Shenk et al. ........... 364/571.02 |
| 4,925,305 A | 5/1990 | Erickson ..................... 356/300 |
| 4,997,280 A | 3/1991 | Norris ......................... 356/308 |
| 5,130,158 A | 7/1992 | Otsubo et al. .............. 426/622 |
| 5,132,538 A | 7/1992 | Norris ......................... 250/339 |

(List continued on next page.)

FOREIGN PATENT DOCUMENTS

| | | |
|---|---|---|
| EP | 0 388 082 | 9/1990 |
| WO | WO 99/40419 | 8/1999 |

OTHER PUBLICATIONS

Randy Nouis, Predicting the Ninety–Fifth Percentile Dust Environment for Passenger Vehicles in the Continental United States, Mar. 1–5, 1993, pp. 1–11.

(List continued on next page.)

Primary Examiner—Diane I. Lee
(74) Attorney, Agent, or Firm—Snell & Wilmer LLP

(57) ABSTRACT

An on-the-go sensor for determining the sugar content of an agricultural product, such as a sugar beet, during harvesting or at other times. The sensor is coupled to a harvester/defoliator and uses a knife to slice a cross-section from the crown of the sugar beet during harvesting. An illumination chamber radiates the exposed crown, and a sensor head receives the reflected radiation. A spectrometer converts the reflected radiation to a spectral signal. A computer digitizes and processes the spectral signal to produce data points relating to the sugar content of the sugar beet. The processing of the data points includes normalization, linearization, and other techniques. One of the techniques eliminates the conventional need to use the spectral signature of a separate physical standard as a reference.

10 Claims, 21 Drawing Sheets

U.S. PATENT DOCUMENTS

| | | |
|---|---|---|
| 5,239,180 A | 8/1993 | Clarke .......................... 250/339 |
| 5,241,178 A | 8/1993 | Shields ........................ 250/339 |
| 5,308,981 A | 5/1994 | Perten .................... 250/339.01 |
| 5,317,524 A | 5/1994 | Das et al. .................... 702/134 |
| 5,327,708 A | 7/1994 | Gerrish ............................ 56/1 |
| 5,351,338 A | 9/1994 | Wigren ....................... 704/219 |
| 5,406,084 A | 4/1995 | Tobler et al. ........... 250/339.01 |
| 5,410,021 A | 4/1995 | Kampen ...................... 530/372 |
| 5,442,438 A | 8/1995 | Batchelder et al. .......... 356/301 |
| 5,448,069 A | 9/1995 | Tobler et al. ........... 250/339.01 |
| 5,472,511 A | 12/1995 | Rayas et al. ................... 127/67 |
| 5,478,748 A | 12/1995 | Akins et al. ................... 436/86 |
| 5,517,302 A | 5/1996 | Stearns et al. .............. 356/326 |
| 5,559,034 A | 9/1996 | Roberts et al. ........... 435/320.1 |
| 5,578,931 A | 11/1996 | Russell et al. .............. 324/536 |
| 5,605,577 A | 2/1997 | Rayas et al. ................... 127/67 |
| 5,617,511 A | 4/1997 | Bigus ............................ 375/26 |
| 5,619,618 A | 4/1997 | Bigus ............................ 395/23 |
| 5,689,333 A | 11/1997 | Batchelder et al. .......... 356/301 |
| 5,697,373 A | 12/1997 | Richards-Kortum et al. ........................... 128/664 |
| 5,751,421 A | 5/1998 | Wright et al. ................ 356/328 |
| 5,755,672 A | 5/1998 | Arai et al. .................... 600/547 |
| 5,844,086 A | 12/1998 | Murray ........................ 530/377 |
| 5,898,792 A | 4/1999 | Oste et al. ................... 382/110 |
| 5,986,749 A | 11/1999 | Wu et al. .................... 356/73.1 |
| 5,991,025 A | 11/1999 | Wright et al. ................ 356/328 |
| 6,001,412 A | 12/1999 | Huber et al. ................. 426/656 |
| 6,005,076 A | 12/1999 | Murray ........................ 530/377 |
| 6,100,526 A * | 8/2000 | Mayes .................... 250/339.11 |
| 6,483,583 B1 * | 11/2002 | Wright et al. ................ 356/326 |

OTHER PUBLICATIONS

C. S. Chang et al., Grain Flow Regulator for Dust Emission Control, Nov.–Dec., 1985, pp. 2059–2062.

Joseph A. Borgia et al., Pressure Drop and Flow Characteristics for a Heavy–Duty Air Filter During Dust Loading, Nov. 16–19, 1987, p. 1–15.

Charles O. Reinhart et al., Measurement of Engine Air Cleaner Efficiency Using Airborne Particle Size Analysis, Sep. 12–15, 1983, pp. 1–8.

Philip C. Williams, et al.; Determination of Protein and Moisture in Wheat and Barley by Near–Infrared Transmission, 1985, pp. 239–244.

K. H. Norris et al., Optimization of Mathematical Treatments of Raw Near–Infrared Signal in the Measurement of Protein in Hard Red Spring Wheat. I. Influence of Particle Size, 1984, pp. 158–165.

Renfu Lu et al., Determination of Firmness and Sugar Content of Apples Using Near–Infrared Diffuse Reflectance, 24 pages.

F. De Lene Mirouze et al., Quantitative Analysis of Glucose Syrups by ATR/FT–IR Spectroscopy, 1993, pp 1187–1191.

Véronique Bellon–Maurel et al., Quantitative Analysis of Individual Sugars during Starch Hydrolysis by FT–IR/ATR Spectrometry. Part I: Multivariate Calibration Study—Repeatability and Reproducibility, 1995, pp 556–562.

Suranjan Panigrahi, et al., On–The–Go Sensing Techniques for Sugar Determination of Sugarbeet in the Field, pp176–178.

E. K. Kemsley et al., Quantitative analysis of sugar solutions using infrared spectroscopy, 1992, pp299–304.

Dr. Daniel S. Humburg et al., Spectral Analysis of Sugar Beet Canopy for Spatial and Temporal Quantification of Sugar Content, Quality, and Disease, Dec. 14, 1999, pp. 1–6.

Dave Berard, Protein Monitor on the Market, 07/97, pp. 18–19.

Carol R. Dumas, New Milestones Monitor Analyzes Grain Quality On The Go, Feb. 14, 1997, pp. 1–4.

Jerry Workman, Jr., A Compact Reference for Practitioners, pp. Contents and 423–435.

Food Processing Automation, May 6, 1990, pp. Table of Contents and 103–114.

Donald A. Burns, Handbook of Near–Infrared Analysis, pp. Contents 53–106.

P. C. Williams et al., Effect of Mutual Interactions on the Estimation of Protein and Moisture in Wheat, Nov. 24, 1982.

Russell Tkachuk, Ph.D., Protein Analysis of Whole Wheat Kernels by Near Infrared Reflectance[1,2].

G. Downey et al., Protein Testing of Wheat by Near Infrared Reflectance.

Frédéric Cadet et al., Direct Spectroscopic Sucrose Determination of Raw Sugar Cane Juices, 1997, pp 166–171.

Gianluigi Marchett, Application of a NIR on–line automatic analyzer system in a beet sugar factory, 1990, pp 210–215.

Nils Berding et al., Crop Ecology, Production & Management, 1991, pp1017–1023.

Nils Berding et al., Near Infrared Reflectance Spectroscopy for Analysis of Sugarcane from Clonal Evaluation Trials: II. Expressed Juice, 1991, pp 1024–1028.

Roberto Giangiacomo et al., Near Infrared Spectrophotometric Determination of Individual Sugars in Aqueous Mixtures, 1986, pp 679–683.

Stephen R. Delwiche et al., Classification of Hard Red Wheat by Near–Infrared Diffuse Reflectance Spectroscopy, 1993, pp. 29–35.

Huaipu Song et al., Neural Network Classification of Wheat Using Single Kernal Near–Infrared Transmittance Spectra, Oct. 1995, pp. 2927–2934.

Stephen R. Delwiche, Single Wheat Kernel Analysis of Near–Infrared Transmittance: Protein Content, 1995, pp. 11–16.

Philip C. Williams, Application of Near Infrared Reflectance Spectroscopy to Analysis of Cereal Grains and Oilseeds, 1975, pp. 561–576.

Near–Infrared Reflectance Method for Protein Determination, pp. 1–2.

Near–Infrared Method for Protein Content in Whole–Grain Wheat, pp. 1–3.

Innovative Protein Monitoring, pp. 1–2.

File History—U.S. Appl. No. 5,751,421.

J. Sorvaniemi et al., Using Partial Least Squares Regression and Multiplicative Scatter Correction of FT–NIR Data Evaluation of Wheat Flours, 1993, pp 251–258.

Suming Chen et al., "Neural Network Analysis of Sugar Content in Fruit Juice", Jul. 18–21, 1999, pp. Title page thru 12.

Renfu Lu et al., "Determination of Sugar Content and Firmness of Apples Using Near–Infrared Diffuse Reflectance", Jul. 9–12, 2000, pp. Title page thru 16.

K. J. Kaffka et al., "Attempts to Determine Oil, Protein, Water and Fiber Content in Sunflower Seeds by the NIR Technique", 1983, pp. 117–119.

Essex E. Finney, Jr. et al., "Determination of Moisture in Corn Kernels by Near–Infrared Transmittance Measurements", 1978, pp. 581–584.

Wang–Sheng Li et al., "Determination of Rough Rice Quality by a Portable Near–Infrared Spectroscopy", 1997, (5) pages.

D. T. Lamb et al., "Moisture Determination in Single Soybean Seeds by Near–Infrared Transmittance", 1991, pp. 2123–2129.

P. C. Williams et al., "Influence of Temperature on Estimation of Protein and Moisture in Wheat by Near–Infrared Reflectance", 1982, pp. 473–477.

D. Wang et al., "Effect of Wheat Kernel Size and Orientation on Reflectance Spectra and Single Kernel Color Classification", 1997, pp. 1–34.

S. R. Delwiche, "Measurement of Single–Kernel Wheat Hardness Using Near–Infrared Transmittance", 1993, pp. 1431–1437.

M. R. Campbell et al., "Whole Grain Analysis in Maize Using Near–Infrared Transmittance Spectroscopy", 1997, pp. 300–303.

Sterner et al., "Infrared Reflectance Spectroscopy for Estimation of Moisture of Whole Grain", 1977, pp. 345–351.

F. E. Dowell et al., "Automated Single Wheat Kernel Quality Measurement Using Near–Infrared Reflectance", 1997, pp. 1,3,5,7, and 9.

B. G. Osborne, "Recent Progress in the Application of NIR to the Measurement of Quality Parameters in Flour", 1982, pp. 577–581.

J. S. Shenk, "How NIR Can Help in Measuring Forage Quality for Breeding and Utilization Programs", (3) pages.

Gerard Downey, "Estimation of Moisture in Undried Wheat and Barley by Near Reflectance", 1985, pp. 951–958.

Doninique Bertrand et al., "Application of Principal Component Analysis to the Prediction of Lucerne Forage Protein Content and in vitro Dry Matter Digestibility by NIR Spectroscopy", 1987, pp. 299–307.

Shuso Kawamura et al., "Determining Undried Rough Rice Constituent Content Using Near–Infrared Transmission Spectroscopy", 1997, pp cover, 1,3,5, and 7.

Holger M. Jaenisch et al., "Instrumentation to Measure the Near–IR Spectrum of Small Fruits", 1990, pp. 162–166.

Paul Geladi et al., "Partial Least–Square Regression: A Tutoria", 1985, pp. 1–17.

Constantinos Goutis, "Second–Derivative Functional Regression with Applications to Near Infra–Red Spectroscopy", 1998, pp. 103–114.

Milling Feed and Fertiliser, "FMBRA takes the Grind out of Measuring Moisture", pp. 34–35.

John S. Shenk et al., "Near Infrared Reflectance Analysis with Single–and Multiproduct Calibrations", 1993, pp. 582–584.

D.T. Williams et al., "The Derivative Spectrometer", 1970, pp. 1597–1605.

F. E. Barton et al., "The Calibration of NIR Reflectance Spectrometer for the Determination of Diverse Compositional Parameters", 1988, pp. 768–773.

R. J. Barnes et al.; "Standard Normal Variate Transformation and De–Trending of Near–Infrared Diffuse Reflectance Spectra", 1989, pp. 772–777.

Kurt C. Lawrence et al., "Sensing Wheat Moisture Content Independent of Density", 1997, pp Cover Page, 1,3,5,7,9, 11,13 and 15.

Abraham Savitzky et al., "Smoothing and Differentiation of Data by Simplified Least Squares Procedures", 1964; pp. 1627–1639.

Principle Introduction to Protronics, (8) pages.

"Comments on the Savitzky–Golay Convolution Method for Least–Square Fit Smoothing and Differentiation of Digital Data", 1978, pp1383–1386.

Gerald S. Birth et al., "Interaction Between Light and Natural Materials: Laboratory Demonstrations", (4) Cover Pages, and pp1–36.

Gerald S. Birth, "How Light Interacts with Foods", (6) pages.

H. Martens et al., "Partial Least Squares Regression: A New Two–Stage NIR Calibration Method", 1982, pp607–647.

Tormod Næs et al., "Comparison of Multivariate Calibration and Discriminant Analysis in Evaluating NIR Spectroscopy for Determination of Meat Tenderness", 1996, pp350–357.

* cited by examiner

US 6,851,662 B2

ON-THE-GO SUGAR SENSOR FOR DETERMINING SUGAR CONTENT DURING HARVESTING

REFERENCE TO RELATED APPLICATIONS

The present application is also a division of U.S. patent application Ser. No. 09/758,392, filed on Jan. 12, 2001, now U.S. Pat. No. 6,624,888, which clams the benefit U.S. provisional patent application Ser. No. 60/175,636, filed Jan. 12, 2000, and entitled "On-The-Go Sugar Sensor for Determining Sugar Content During Harvesting," which is incorporated herein by reference.

The present application is related to the following applications, all of which are incorporated herein by reference: U.S. provisional patent application Ser. No. 60/164,161, filed Nov. 8, 1999, and entitled "Optical Analysis of Grain Stream"; and U.S. patent application of Suranjan Panigrahi and Guangjun Zhang, filed on Nov. 7, 2000, and entitled "Optical Sensor for Analyzing a Stream of an Agricultural Product to Determine Its Constituents."

FIELD OF THE INVENTION

The present invention relates to an apparatus for measuring constituents of sugar beets during harvesting or in the field after harvesting. Additionally, the present invention relates to a method and apparatus using a near-infrared (NIR) spectrometer and optical analysis in combination with a sugar beet harvester/defoliator for real-time quality analysis of sugar beets. This invention may also be used for determination of sugar content of other sugar-containing agricultural products such as grapes, grapefruits, oranges, or other fruits.

BACKGROUND OF THE INVENTION

Food producers and others often analyze the major constituents, such as sugar content and moisture, of certain agricultural products including sugar beets, grapes, and grapefruits. This analysis can be used for developing new hybrid species of crops. Moreover, with the advent of precision farming, it is desirable to obtain information relating to quality, such as sugar content, of an agricultural product being harvested along with yield (quantity) information. At present, technologies are available to determine the sugar content of sugar-containing agricultural products in laboratory conditions or in a processing plant. However, it is desirable to obtain quality information during harvesting in order to manage and plan crop production for consistent quality. Therefore, a need exists for a sensor with or without a harvester to operate in a field environment and which is also capable of determining sugar content in real-time, near real-time, or in a quick manner.

SUMMARY OF THE INVENTION

A device consistent with the present invention is used for determining sugar content of an agricultural product while being harvested or in the field condition. The device includes a sample preparation mechanism attached to a harvester/defoliator for use with a received agricultural product during harvesting to create an exposed sample of the agricultural product. An illumination chamber radiates the exposed sample, and a sensor receives radiation from the exposed sample. A spectrometer converts the radiation into a corresponding spectral signal, and a computer receives the spectral signal and processes it to determine an indication of sugar content of the agricultural product.

A method consistent with the present invention processes a spectral signal to predict sugar content of an agricultural product. The method includes receiving a light signal from an agricultural product and converting the light signal into a spectral signal. The spectral signal is digitized to produce a plurality of data points, which are then processed using dark signal values and a reference signal value to produce a plurality of normalized data points. The normalized data points have values related to sugar content of the agricultural product and can be used to predict the sugar content using various prediction techniques.

BRIEF DESCRIPTION OF THE DRAWINGS

The accompanying drawings are incorporated in and constitute a part of this specification and, together with the description, explain the advantages and principles of the invention. In the drawings.

DETAILED DESCRIPTION

Overview

Figure 1:
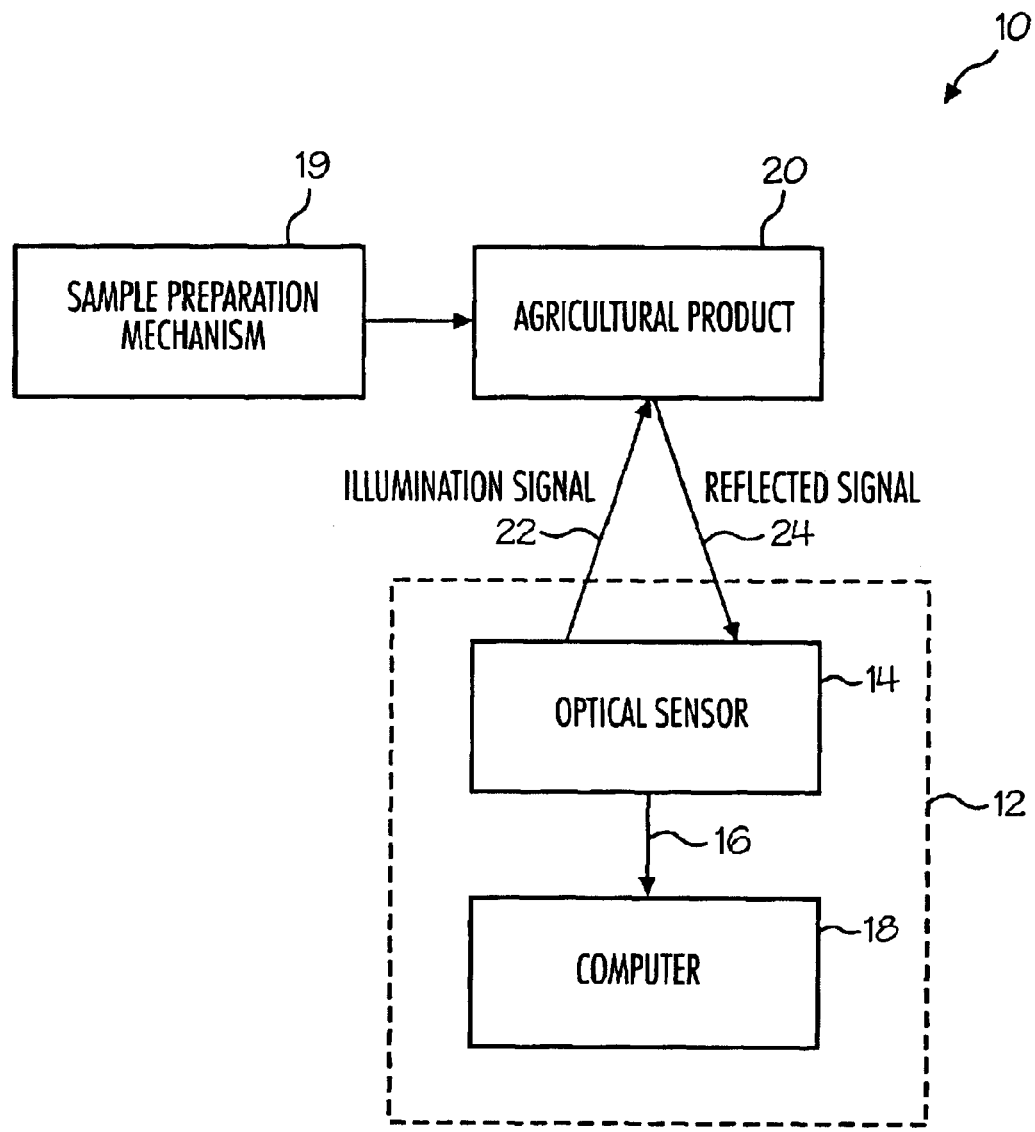
FIG. 1 is a diagram illustrating use of an optical sensor for predicting sugar content of an agricultural product.

FIG. 1 illustrates a system 10 consistent with the present invention for using an optical sensor 14 to predict the sugar content or other constituent of an agricultural product 20. In system 10, optical sensor 14 provides an illumination signal 22 onto agricultural product 20. Optical sensor 14 receives a reflected signal 24 including at least a portion of illumination signal 22 reflected from agricultural product 20. Optical sensor 14 converts the received reflected signal 24 into a corresponding electronic signal. The electronic signal is transmitted by a link 16 to a computer 18, where it is digitized and processed in order to determine and predict sugar content of agricultural product 20. Optical sensor 14 and computer 18 are illustrated within a unit 12, since they may be combined into a single physical unit or maintained as separate units depending upon requirements of a particular application.

Optical sensor 14 along with associated computer 18 can be used to analyze and predict sugar content of a wide variety of agricultural products 20. In an exemplary embodiment, it is used to predict sugar content of a sugar beet. However, it can be used to predict sugar contents of the many other types of agricultural products where it may be important or desirable to have an indication of sugar content. For example, it can be used to predict sugar content of citrus fruits such as oranges, grapefruits, and other such fruits. In addition, it can be used to predict sugar content of grapes, which may be useful for analysis by wineries.

For certain agricultural products such as sugar beets and grapefruits, optical sensor 14 uses an invasive technique, as those agricultural products have an exterior layer that must be removed in order to illuminate a main body of the agricultural product. For those agricultural products, the system uses a sample preparation mechanism 19 for exposing a sample of agricultural product 20 for radiating by illumination signal 22. The term "exposed sample" refers to an exposed portion of an agricultural product created by a sample preparation mechanism. For agricultural products such as sugar beets, as explained below, optical sensor 14 and associated computer 18 can use sample preparation mechanism 19 to prepare a sample and predict sugar content of the sugar beets during harvesting or in the field. This provides for real-time or near real-time indications of sugar content during harvesting and further provides for the ability to generate a map of sugar content across an entire field of an agricultural product.

With other agricultural products such as grapes, the system can use a non-invasive technique to predict sugar content by illuminating the exterior of grapes and receiving a reflected signal. Since grapes have at least a semi-transparent exterior, at least a portion of the radiation will be reflected from the main, interior portion of the grapes. This technique thus provides an advantage of avoiding destruction of the grapes or other agricultural products in order to predict sugar content.

Depending upon the particular application, as indicated, optical sensor 14 and computer 18 can be implemented as a single physical unit 12 or as separate units connected by electronic link 16. These variations on the configuration provide for the advantage of implementing the system within a wide variety of applications. For example, as explained below, optical sensor 14 and computer 18 can be mounted on an implement for harvesting sugar beets and thus sample and predict sugar content of the sugar beets during the harvesting. For citrus fruits and grapes, optical sensor 14 and computer 18 can be implemented within a single unit 12, such as a hand-held or portable unit, for sampling and predicting sugar content of the fruits and grapes, easily carried among fruit trees of an orchard or grapevines of a winery. The hand-held unit may include one physical unit or separate components linked together.

The system can also be used in other applications, such as in a food processing facility for sampling and predicting sugar content of an agricultural product on an assembly line within the facility. This provides the advantage of obtaining an indication of sugar content of an agricultural product during the food manufacturing process in real-time, near real-time, or in a quick manner. In addition, the obtained indication of sugar content can be used within the food processing facility or other application in order to categorize a particular quality of an agricultural product. For example, sugar beets having a higher sugar content can be directed within a sugar refinery to indicate a sugar having a higher quality, while sugar beets having a lower sugar content can be directed within the sugar refinery to indicate sugar having a lower quality.

Although a particular embodiment uses reflected signal 24, the same components and processing can be used on light transmitted through particular agricultural products, such as grapes, that can pass a certain amount of light. For those agricultural products, the system can alternatively transmit light through the agricultural product by positioning of separate components in optical sensor 14 for generating illumination signal 22 and receiving a transmitted light signal passed through the agricultural product. This option provides more versatility in terms of positioning the physical components for sampling a particular agricultural product using a light signal either transmitted through or reflected from an agricultural product.

Optical Sensor System

Figure 2:
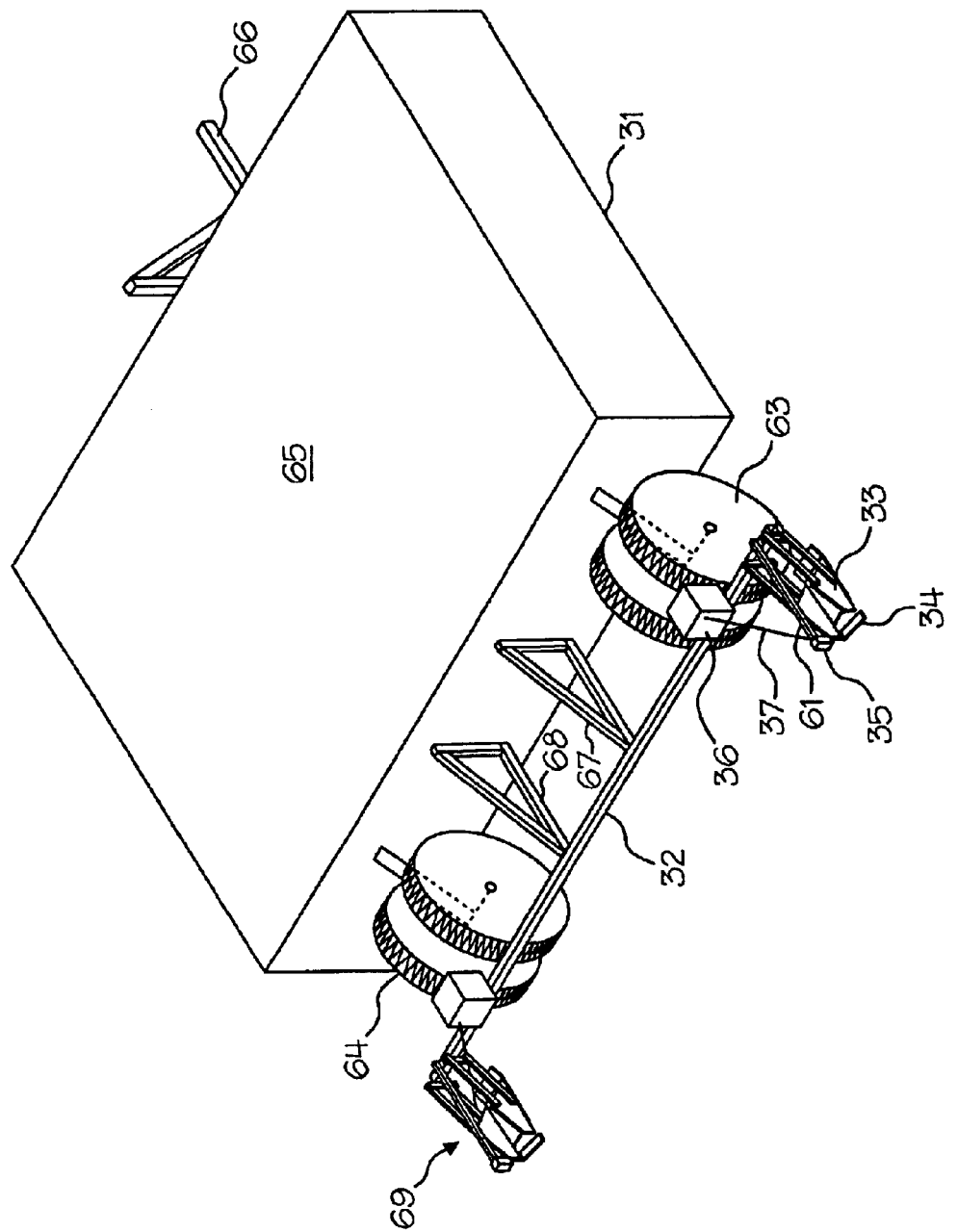
FIG. 2 is a diagram of an on-the-go optical sensor mounted on a sugar beet defoliator.

FIG. 2 shows a typical sugar beet defoliator 65, which may be used with the optical. sensor. Defoliator 65 is used to remove plant materials from the top or crown of sugar beet roots before they are gathered by a sugar beet harvester/lifter. A typical defoliator 31 includes a beam 32, a sliding mechanism 33, and a knife 34. The optical sensor includes a sensing module 35 and a computer 36. Sensing module 35 sends an acquired signal through a fiber optic cable 37 to computer 36 and is mounted on a supporting beam 61, which is also attached to a cross bar/beam 32. Although shown attached to a defoliator, the optical sensor can alternatively be attached to a harvester/defoliator, and the term "harvester/defoliator" includes a harvester and/or defoliator depending upon, for example, the type of agricultural product being harvested.

Defoliator 65 includes brackets 67 and 68. In addition, it includes one pair of wheels 63 and another pair of wheels 64 for permitting it to traverse a field during harvesting. Defoliator 65 is attached by a hitch 66 to a tractor or other vehicle for pulling it through a field in order to defoliate sugar beets as part of the harvesting process. Harvesting of sugar beets is known in the art with respect to existing harvesters.

Defoliator 65 includes inside of it rotating rubber beaters that remove the green foliage material from the sugar beet. Any remaining foliage material is removed by knife 34. Following the defoliating process, another harvesting unit removes the sugar beets from the soil for being transported to a sugar refinery, or other food processing or storage facility.

Optical sensor 14 and associated computer 18 are mounted in this example to an existing defoliator 65. In particular, cross bar 32 typically contains a plurality of defoliating apparatus such as sliding mechanisms 33 and 69. Each defoliating apparatus may include its own optical sensor and associated computer for sampling and predicting sugar content among a plurality of rows of sugar beets during the harvesting process. The sensor can be integrated with similar or modified configurations on a sugar beet harvester.

Figure 4:
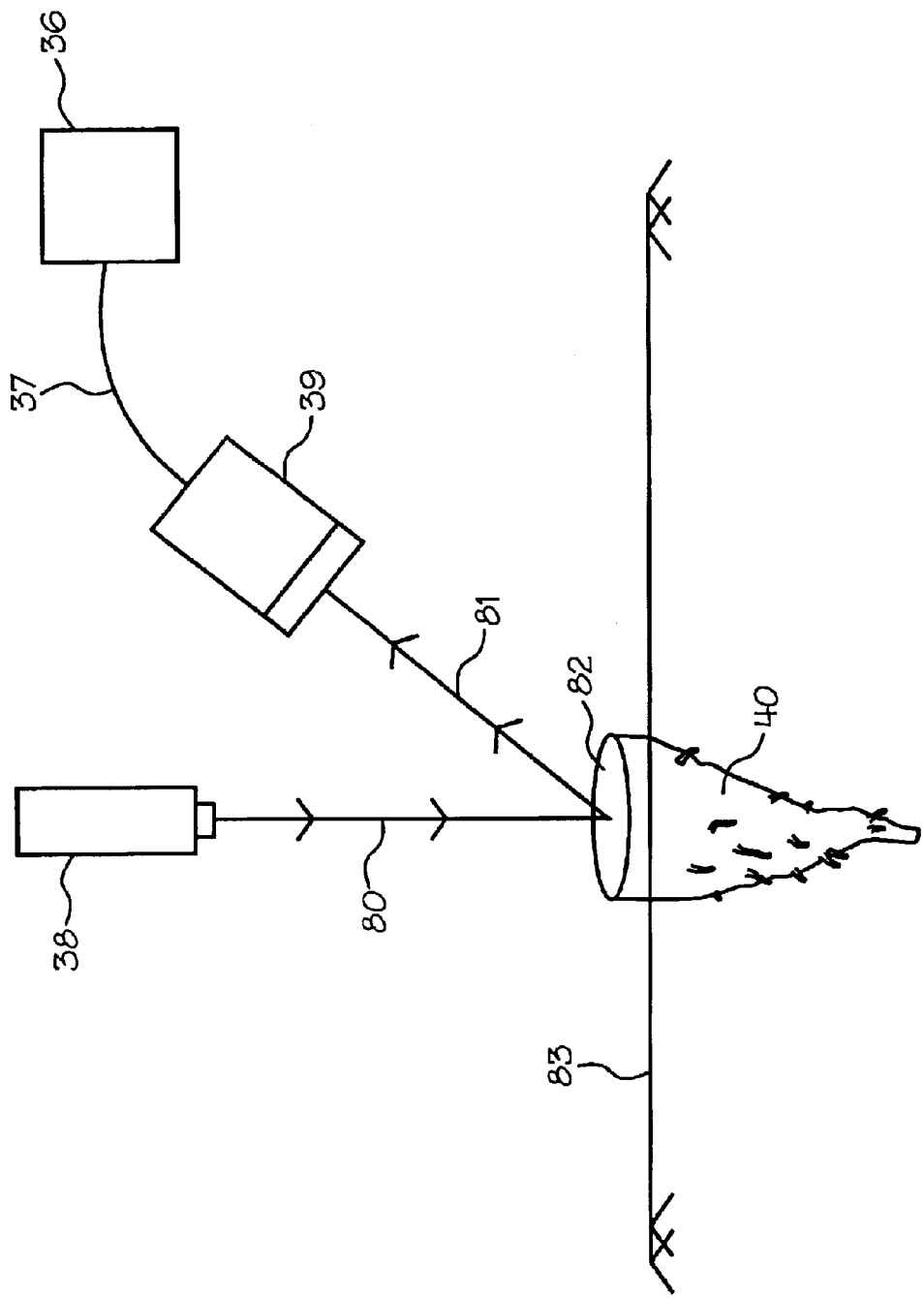
FIG. 4 is a diagram illustrating a sensing process for use in determining sugar content of a sugar beet during harvesting.

This sampling is illustrated in FIG. 4. Immediately after knife 34 removes remaining foliage from the sugar beet and a portion of its crown, a surface 82 is exposed. At that time an illumination chamber 38 in sensing module 35 provides an illumination signal 80 onto surface 82. A sensor head 39 in sensing module 35 detects a reflected signal 81. The term "illumination chamber" includes any apparatus for generating a light signal or radiation for radiating a sample of an agricultural product for analysis, and the term "sensor head" includes any apparatus for receiving a reflected light signal or radiation from an agricultural product and transmitting it onto a fiber optic cable or other light carrier for conversion into a corresponding electrical signal. The terms "light signal" and "radiation" include any visible or invisible light signal. This particular exemplary embodiment uses a light signal in the NIR spectrum, although light signals within other spectrums can be used.

During this sampling process, sugar beet 40 remains within the soil, represented by line 83. Although the harvesting process can generate a significant amount of dust, the sampling of exposed surface 82 occurs immediately after knife 34 slices through the top crown of sugar beet 40. Therefore, exposed surface 82 is sampled and illuminated before any appreciable amount of dust can accumulate on its surface.

Figure 3:
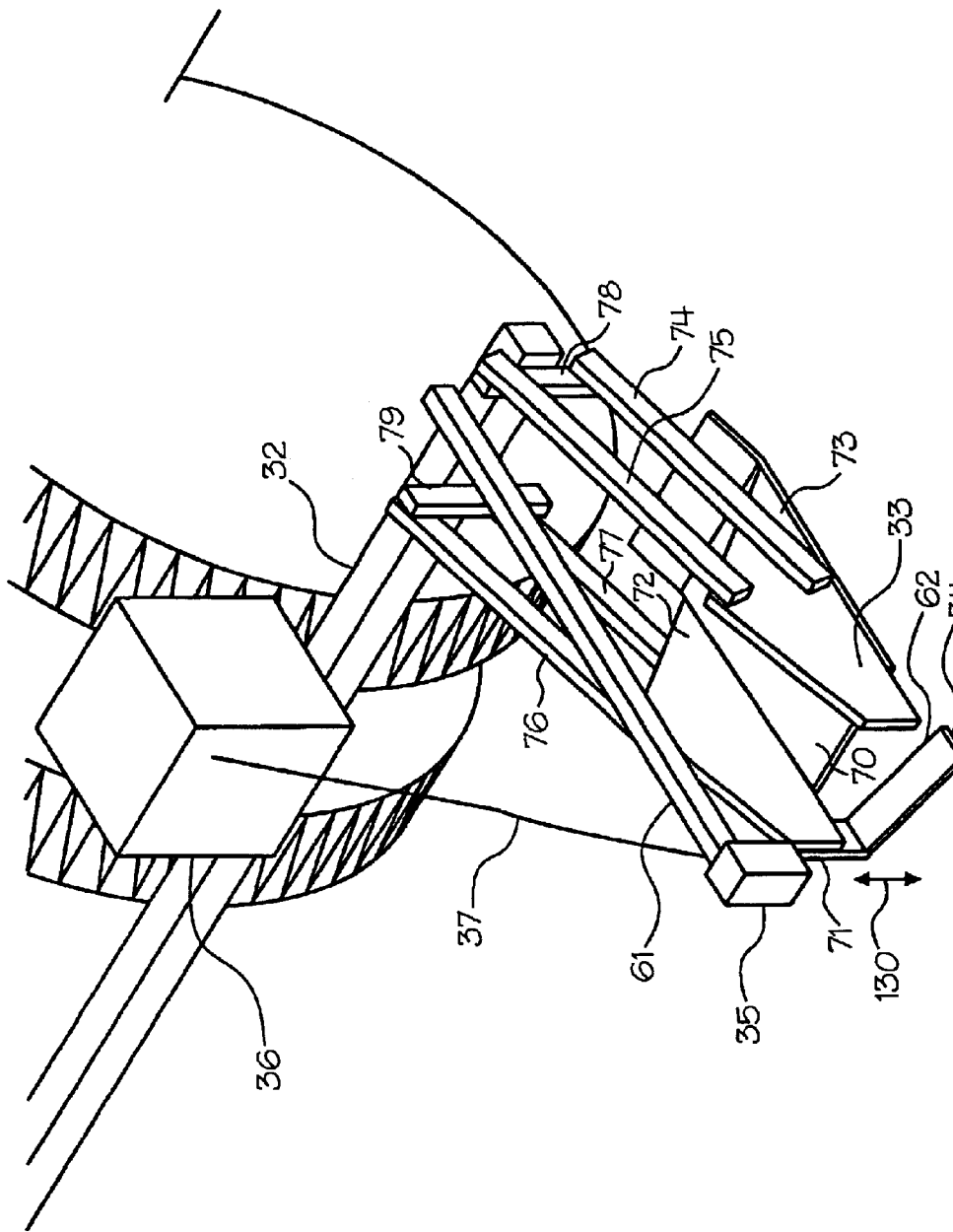
FIG. 3 is a magnified view of the defoliator showing the location of components for the optical sensor.

FIG. 3 shows a magnified view of a portion of the defoliator illustrating the locations of sensing module 35, fiber optic cable 37, and computer 36. The existing defoliating apparatus includes a pair of vertical mounting brackets 78 and 79 mounted to beam 32. The vertical mounting brackets 78 and 79 are used to support a plurality of mounting bars 74, 75, 76 and 77 on each defoliating apparatus. Those mounting bars support sides 72 and 73 for a defoliating tray 70. Knife 34 is mounted to side 72 by a sliding bracket 71. Therefore, a position of knife 34 can be adjusted in a vertical direction as shown by arrows 130. During defoliation, front edge 62 of knife 34 slices through a top crown of the sugar beet in order to expose the sugar beet for sampling and analysis.

Figure 5B:
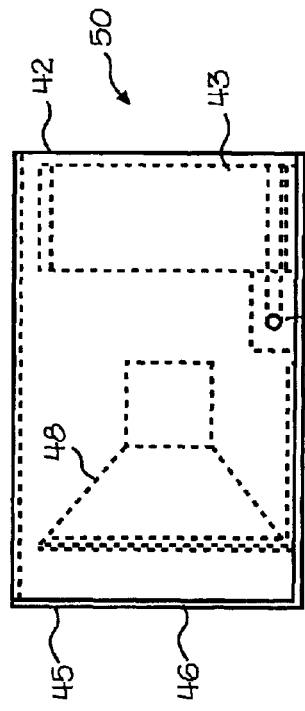
FIGS. 5A–5E are diagrams illustrating an illumination chamber for the optical sensor.
Figure 5E:
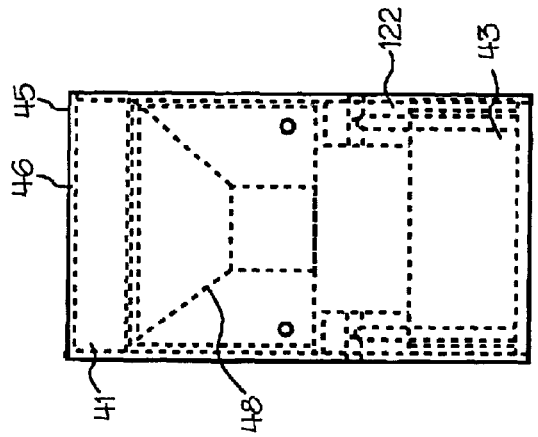
Figure 5D:
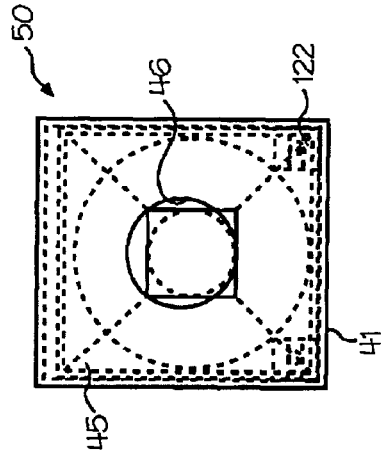
Figure 5A:
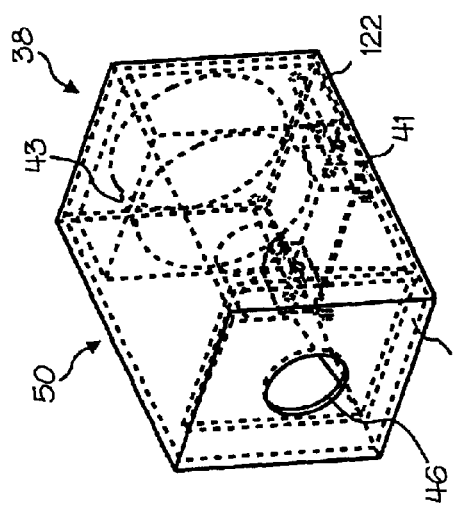
Figure 5C:
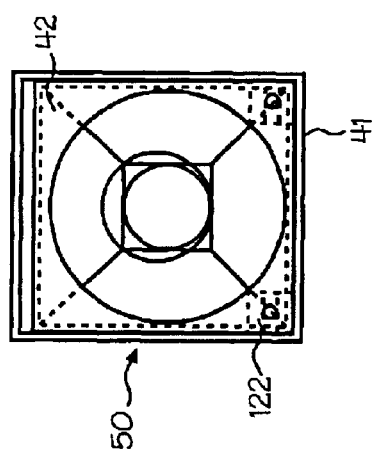

FIGS. 5A–5E are diagrams illustrating the illumination chamber 38. Embodiment 38 is shown with exemplary dimensions in inches. Illumination chamber 38 is shown in a perspective view (FIG. 5A), side view (FIG. 5B), back view (FIG. 5C), front view (FIG. 5D), and bottom view (FIG. 5E). Illumination chamber 38 can include a frame 122 for supporting a fan 43. As an alternative to the fan, other ventilation mechanisms can be used, and the term "ventilation mechanism" includes any device or feature to reduce heat build-up in the illumination chamber.

Frame 122 can be welded or otherwise affixed onto a base plate 41. A light source 48 can likewise be attached in an enclosure 50. The light source 48 includes a removeable light bulb and a holder to hold the light bulb, and the holder is attached to base plate 41. The sides of removeable enclosure 50 can be attached onto base plate 41, affront wall 45, and a rear wall 42. Fan 43 can be removeable within enclosure 50. Enclosure 50 can be formed from metal or other opaque materials for shielding the illumination chamber from ambient light and isolating the light source 48. The enclosure 50, and light source 48 and fan 43, can be joined together with fasteners, adhesives, or in other ways.

Figure 6:
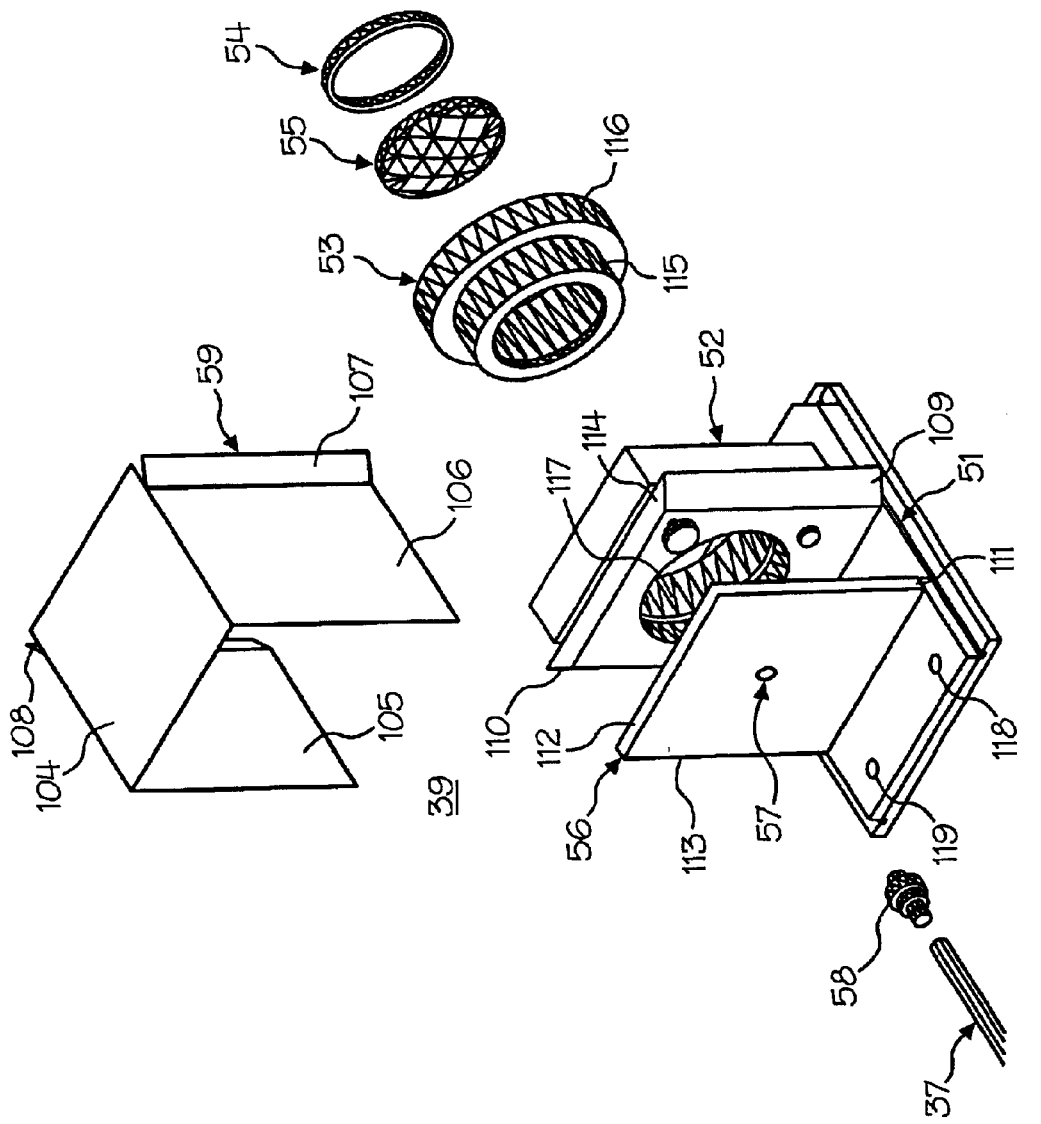
FIG. 6 is a diagram of a sensor head for the optical sensor.

FIG. 6 shows components of sensor head 39. Sensor head 39 has a base platform 51. A front face 52 of the sensor head contain a lens holder 53, which further contains a retaining ring and an optical lens 55. Lens holder 53 includes a first portion 115 and second portion 116. Portion 115 mounts within aperture 117 when in use. Lens 55 is kept in position by a retaining ring 54 at the back of the lens. A rear face 56 of the sensor head is attached to the base platform and contains a hole 57 to accommodate a collimating lens 58 attached to optical fiber 37.

Enclosure 59 includes a top surface 104, and sides 105 and 106. In this example side 105 has a flanged portion 108, and side 106 and a flanged portion 107. When enclosure 59 is mounted on base platform 51, top surface 104 rests flush against surfaces 114 and 112; side 105 and flanged portion 108 rest flush against, respectively, side 113 and angled portion 110; and side 106 and flanged portion 107 rest flush against, respectively, side 111 and angled portion 109. Therefore, when enclosure 59 is mounted on base platform 51, it provides for isolating the received light/radiation in order to help prevent interference from ambient light and maintain the receiving chamber free from dust. Enclosure 59 is painted, for example, black both on the inside and outside to help reduce interference from reflected light within the enclosure. Also, base platform 51 includes apertures 118 and 119 for receiving fasteners in order to secure the receiving unit onto a bracket on a harvester/defoliator.

Optical Sensor Operation

Referring to FIGS. 1–6, the on-the-go system operates as follows. When the defoliator 65 moves, the beaters inside of it crush the leaf material on the top of the sugar beet root. Knife 34 in the defoliator is a knife that already exists in a typical defoliator to remove the crown of the sugar beets during harvesting, and it can also be used as a sample preparation mechanism for a sugar sensor. For sampling, with the forward motion of defoliator 65 in the field, knife 34 moves across the top (crown) of the sugar beet root and cuts out a thin cross-section of the sugar beet root using edge 62. During this process, the sugar beet root is still resting in the ground. The vertical position 130 of knife 34 can be adjusted for preparing an appropriate sample. In this example, the position of knife 34 is adjusted so as to cut approximately a one to one-and-a-half inch thick cross-section from the top (crown) of the sugar beet root, thus exposing an open surface 82 on the root 40. As an alternative to knife 34, other cutting apparatus can be used to prepare a sample of a sugar beet or other agricultural product, and the term "cutting apparatus" includes any instrument or device for exposing a main body of an agricultural product for sampling.

A light signal, in this example NIR radiation, from illumination chamber 38 radiates the exposed surface 82 of the sugar beet root and the reflected radiation from that surface passes through front face of sensor head 39. The reflected radiation passes through optical lens 55 inside the sensor head and is received by collimating lens 58 located on rear wall 56. The received reflected signal is transmitted through fiber optic cable 37 to an NIR spectrometer associated with computer 36. The spectrometer contains, for example, a diffraction grating and a series of Indium Gallium Arsenide (InGAAS) photodetectors. The spectrometer may also be thermo-electrically cooled. The spectral signature acquired by the spectrometer ranges from 900–1700 nanometers (nm) in this example for sugar beets. The acquired spectral signal is further processed to determine sugar content. Depending on the sample preparation mechanism, the spectral signal could also be generated by passing radiation through a an agricultural product or a sample of it.

The term "sample preparation mechanism" includes any device for exposing a portion of an agricultural product for receiving, and reflecting or transmitting, radiation. Although shown in this example as a knife on a defoliator, a particular implementation of a sample preparation mechanism may depend upon, for example, the harvesting process for an agricultural product, the type of agricultural product, and the location of sampling other than harvesting such as in a food processing plant.

Computer Hardware and Related Components

Figure 7:
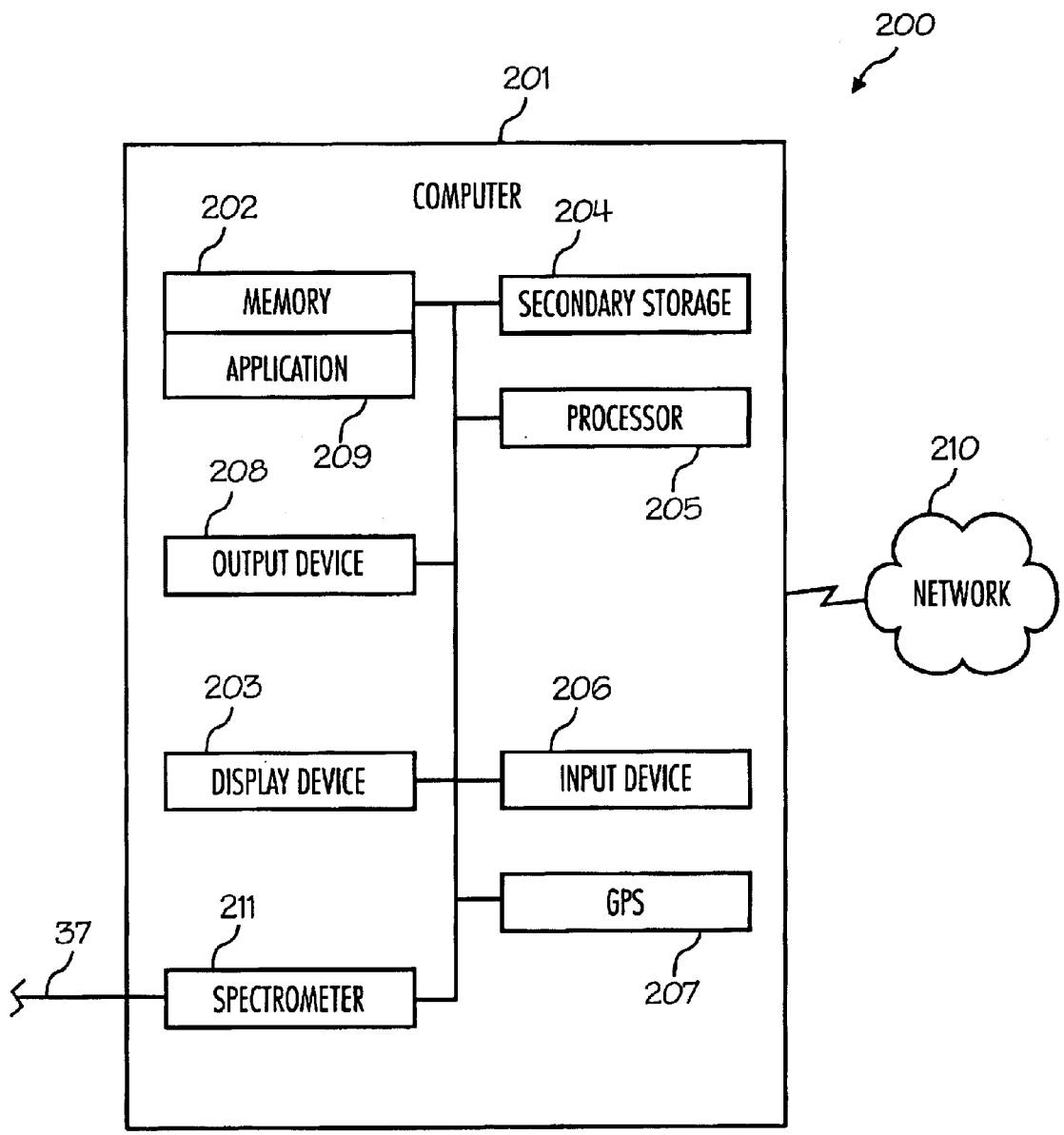
FIG. 7 is a diagram of exemplary components of a computer for analyzing a signal received from the optical sensor for predicting sugar content or other constituents.

FIG. 7 depicts a data processing system 200 with a computer 201 illustrating exemplary hardware and peripheral components of computer 36. Computer 201 may include a connection with a network 210 such as the Internet or other type of network, and it can include a wireline or wireless connection with the network. For example, if the optical sensor is used in a food processing facility, the computer may include a wireline connection with a network to transmit stored sugar content data. On the other hand, if the optical sensor is used on a sugar beet harvester, the computer may include a wireless connection with a network to transmit the sugar content data to a food processing facility or other location.

Computer 201 typically includes a memory 202, a secondary storage device 204, a processor 205, an input device 206, a global positioning system (GPS) 207, a display device 203, and an output device 208. A GPS is known in the art and provides approximate longitude and latitude coordinates for its geographic location based upon triangulation of signals received from GPS satellites. Memory 202 may include random access memory (RAM) or similar types of memory, and it may store one or more applications 209, including a web browser, for execution by processor 205. Secondary storage device 204 may include a hard disk drive, floppy disk drive, CD-ROM drive, or other types of nonvolatile data storage. Processor 205 may execute applications or programs stored in memory 202 or secondary storage 204, or received from the Internet or other network 210. Input device 206 may include any device for entering information into computer 201, such as a keyboard, key pad, cursorcontrol device, or touch-screen. Display device 203 may include any type of device for presenting visual information such as, for example, a computer monitor, flat-screen display, or display panel. Output device 208 may include any type of device for presenting a hard copy of information, such as a printer, and other types of output devices include speakers or any device for providing information in audio form.

Computer 201 also includes in this example a spectrometer 211 connected with fiber optic cable 37. Spectrometers are known in the art, and the term "spectrometer" refers to any type of component for converting a light signal into a corresponding electrical signal at one or multiple wavelengths. Therefore, spectrometer 211 receives the light signal from fiber optic cable 37, converts it into a corresponding analog electrical signal, and digitizes the analog signal through an analog-to-digital (A/D) converter to produce a digitized version of the raw reflected signal. The A/D conversion can be implemented as part of spectrometer 211 or as a separate component such as a controller card in computer 201. Also, spectrometer 211 can be implemented as part of computer 201, as shown, or as a separate physical component electronically linked with computer 201. Also, depending upon the agricultural product to be analyzed, spectrometer 211 can be calibrated/programmed to convert a range of the light signal between particular wavelengths. The range of the light signal used for prediction of sugar content may be different for various types of agricultural products as determined through empirical evidence.

Although computer 201 is depicted with various components, one skilled in the art will appreciate that this computer can contain additional or different components. In addition, although aspects of an implementation consistent with the present invention are described as being stored in memory, one skilled in the art will appreciate that these aspects can also be stored on or read from other types of computer program products or computer-readable media, such as secondary storage devices, including hard disks, floppy disks, or CD-ROM; a carrier wave from the Internet or other network; or other forms of RAM or ROM. The computer-readable media may include instructions for controlling a computer system, such as computer 201, to perform a particular method.

Figure 9:
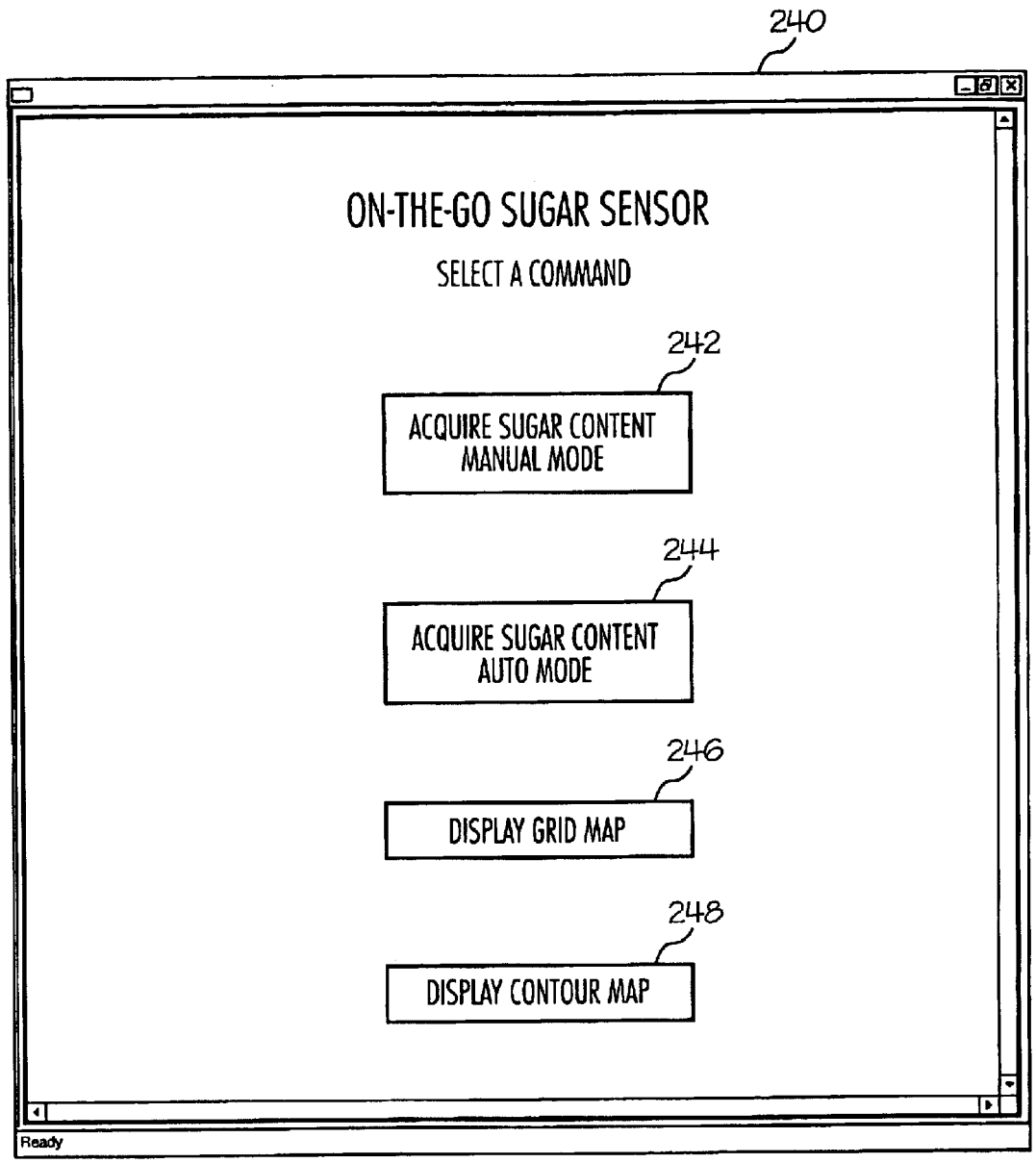
FIG. 9 is a diagram of a main screen for the user to select and enter a command into the system.
Figure 13:
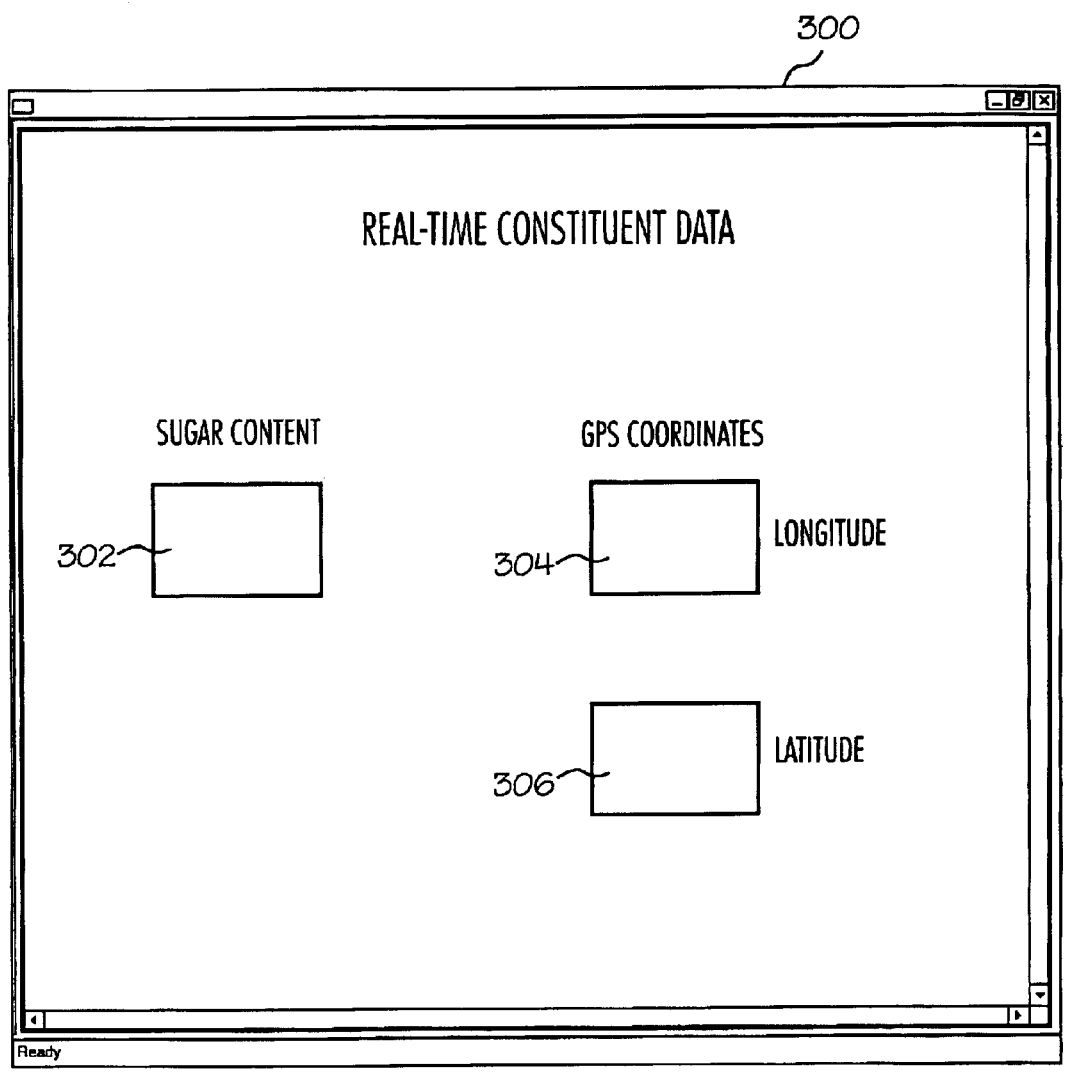
FIG. 13 is a diagram of a screen for displaying in real-time or near real-time an indication of sugar content and corresponding geographical location of an analyzed agricultural product.
Figure 15:
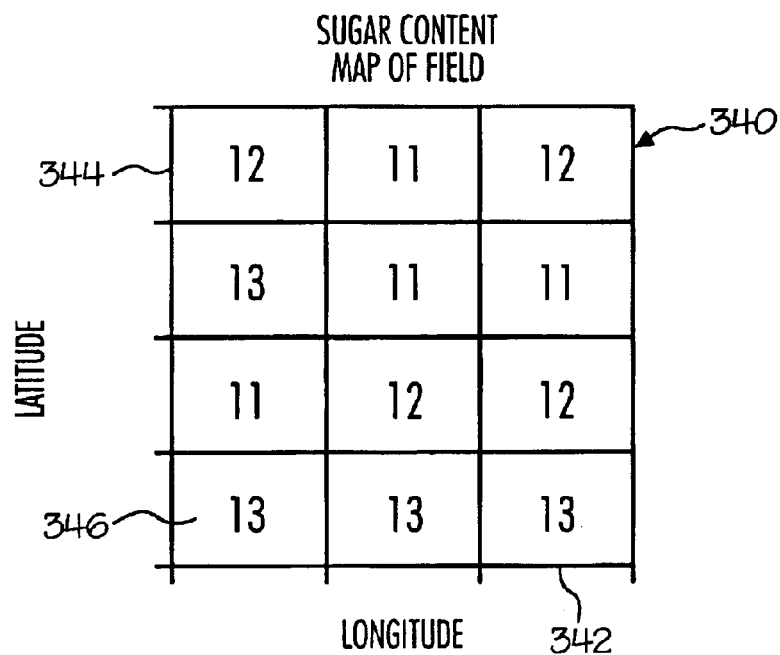
FIG. 15 is a diagram of a grid map indicating sugar content of a field of agricultural products.
Figure 16:
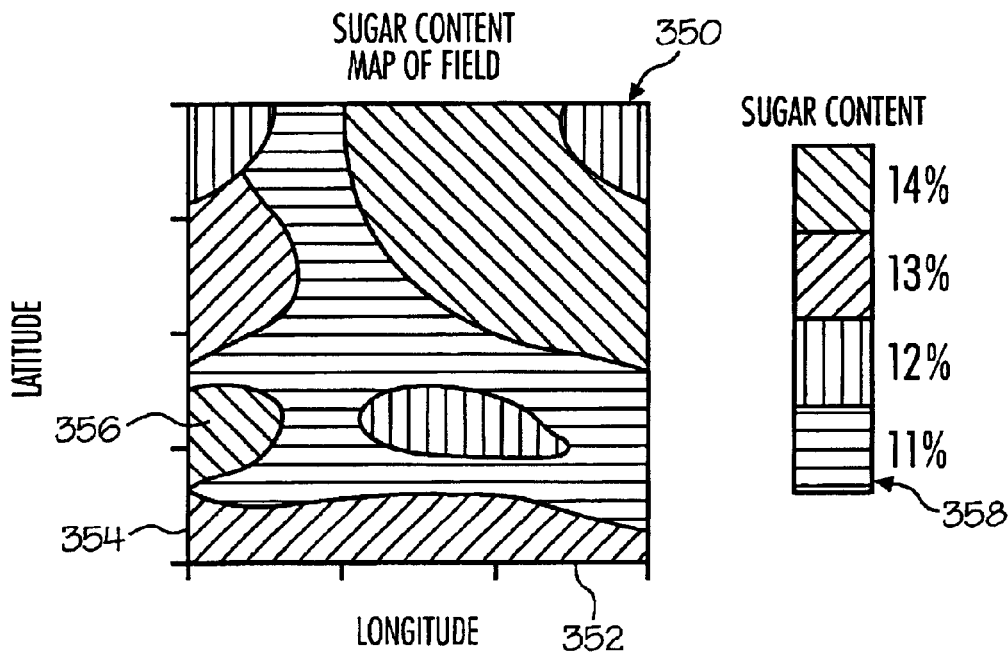
FIG. 16 is a contour map indicating sugar content of a field of agricultural products.

Computer 201 displays a screen through which users interact with the system. FIG. 9 is a diagram of a screen illustrating how a user can interact with the system, and this screen may be displayed on display devices associated with computer 201. Computer 201 can also display a screen to present information, such as sugar content data to or maps of sugar content access a field, and examples of such screens are shown in FIGS. 13, 15, and 16. The term "screen" refers to any visual element or combinations of visual elements for displaying information; examples include, but are not limited to, user interfaces on a display device or information displayed in web pages or in windows on a display device. The screens may be formatted, for example, as web pages in HyperText Markup Language (HTML), or in any other suitable form for presentation on a display device depending upon applications used to interact with the system.

The screens include various sections, as explained below, to provide information or to receive information or commands. The term "section" with respect to screens refers to a particular portion of a screen, possibly including the entire screen. Sections are selected, for example, to enter information or commands or to retrieve information or access other screens. The selection may occur, for example, by a using a cursor-control device to "click on" or "double click on" the section; alternatively, sections may be selected by entering a series of key strokes or in other ways such as through voice commands or use of a touch screen. In addition, although the screens shown in FIGS. 9, 13, 15, and 16 illustrate a particular arrangement and number of sections, other arrangements are possible and different numbers of sections in the screen may be used to accomplish the same or similar functions of displaying information and receiving information or commands. Also, the same section may be used for performing a number of functions, such as both displaying information and receiving a command.

The processing to support the screens is shown in the flow charts of FIGS. 8, 10, 11, and 14 specifying various routines. The processing may be implemented in software, such as software modules, for execution by processor 205 in computer 201 or other machines.

Software Processing

Figure 8:
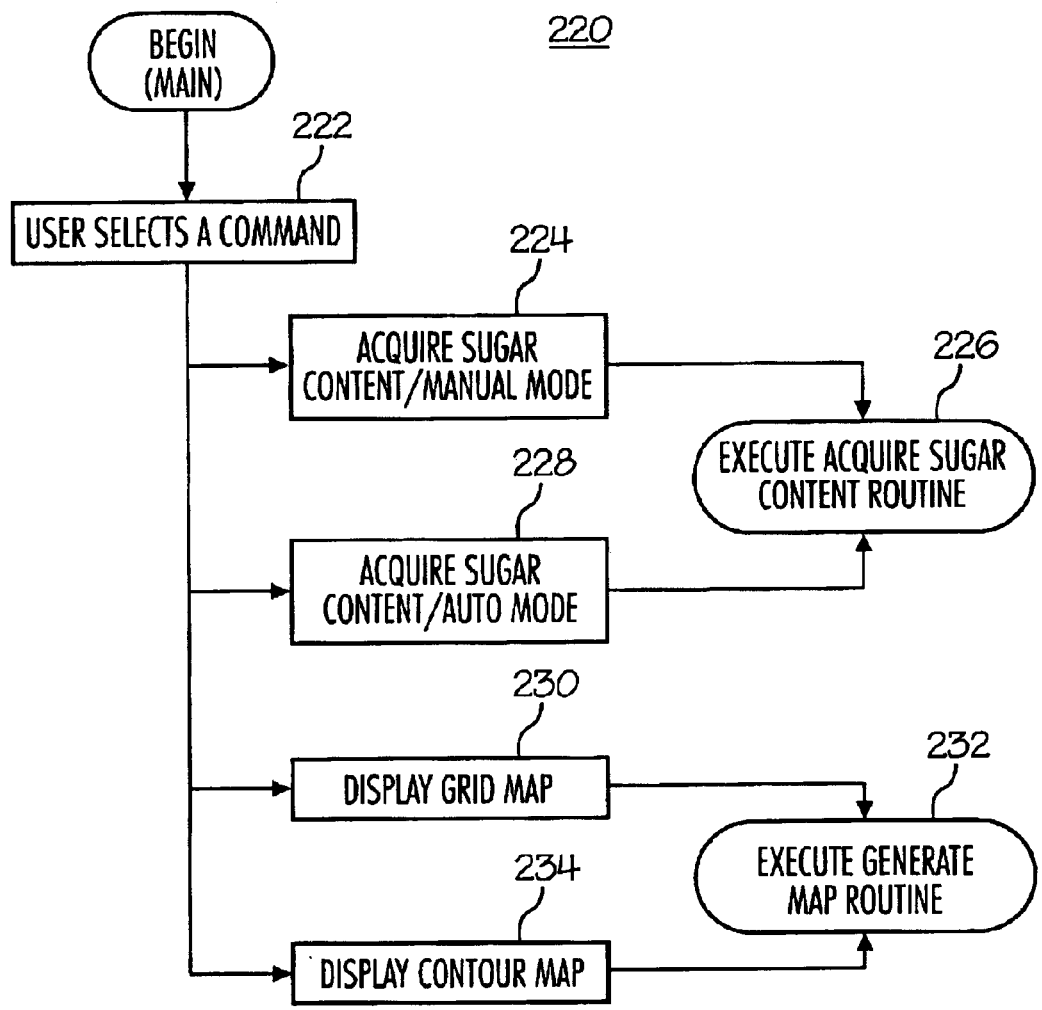
FIG. 8 is a flow chart of a main method for a user to select a command for the system.

FIG. 8 is a flow chart of a main routine 220 for receiving a command entered by a user. As part of main routine 220, computer 36 may display a main screen 240 as shown in FIG. 9. Main screen 240 includes sections for selection by the user in order to enter a command. In particular, in this example it includes a section 242 for selection by the user to acquire sugar content in a manual mode, a section 244 to acquire sugar content in an automatic mode, a section 246 to display a grid map of acquired sugar content, and a section 248 to display a contour map of stored sugar content. The grid and contour maps are further explained below.

In routine 220, the user selects a command by selecting one of the sections in screen 240 (step 222). Alternatively, the user may enter a command through other ways, such as a particular key stroke. The system then determines the entered command. If the user entered a command to acquire sugar content in the manual mode or the automatic mode (steps 224 and 228), the system executes an acquire sugar content routine (step 226). If the user entered a command to display a grid map or a contour map (steps 230 and 234), the system executes a generate map routine (step 232).

Figure 10:
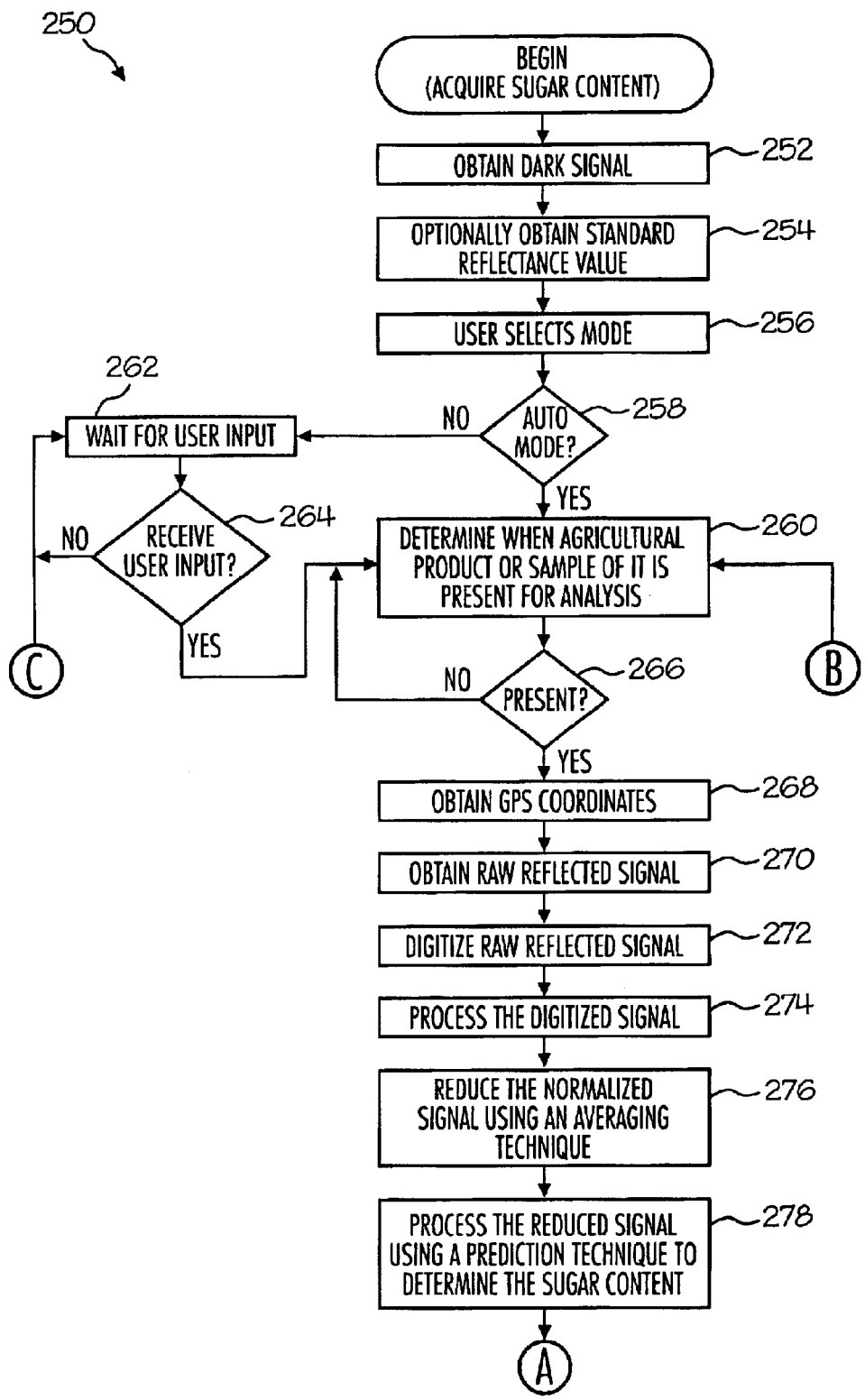
FIGS. 10 and 11 are a flow chart of an acquire sugar content routine to predict sugar content based upon a signal received from the optical sensor.
Figure 11:
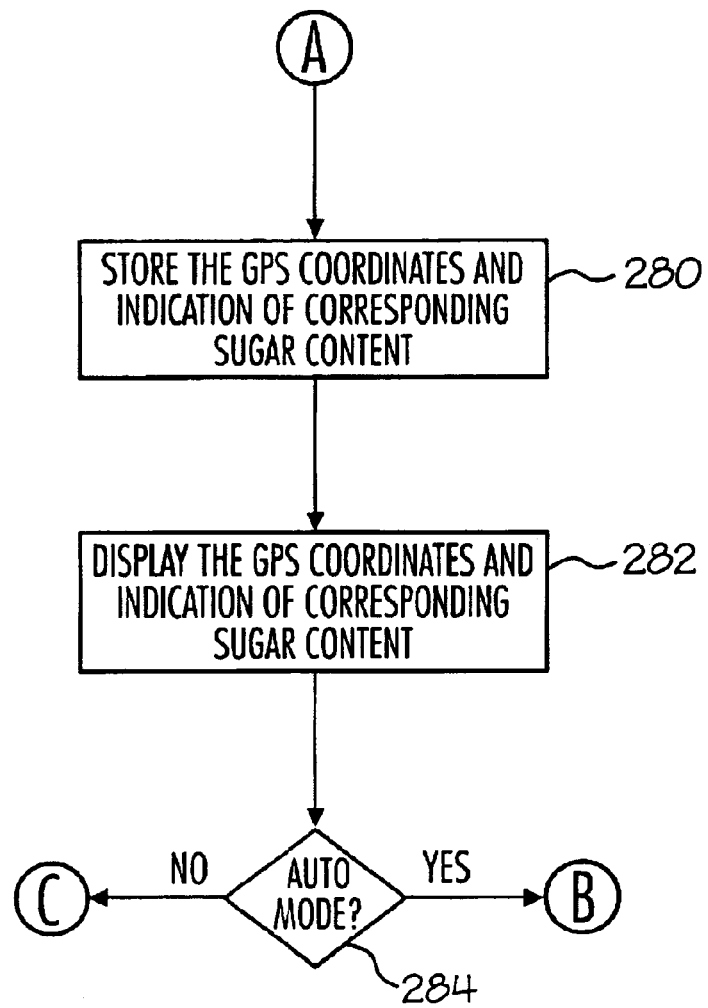

FIG. 10 is a flow chart of an acquire sugar content routine 250 executed in step 226 in response to the user entering a command to acquire sugar content. In routine 250, the system first obtains the dark signal (step 252). The dark signal is typically predetermined and stored in the system each time the system is used. The system optionally obtains a standard reflectance value (step 254); some embodiments do not necessarily require use of the standard reference value, as explained below. The standard reflectance value may be based upon the type of agricultural product to be analyzed. In this example the cross-section of the sugar beet has a white surface and therefore a white reflectance standard value is used, such as the white reflectance standard from Lab Sphere (NH). Other standards for reflectance of a white surface may be used. Also, for agricultural products having different colored surfaces to be analyzed, reflectance standards for other such colors may be used.

The user then selects a mode through a selection of sections 242 or 244 in screen 240 (step 256). The system determines whether the user selected the manual mode or the automatic mode by determining which section was selected (step 258). The manual mode means that the system samples and predicts sugar contents of sugar beets or other agricultural products in response to user input. The automatic mode means that the system samples and predicts sugar content of sugar beets or other agricultural products when detected by the system. Therefore, in the automatic mode the system can repeatedly sample and predict sugar content of sugar beets as detected during harvesting.

For the manual mode the system waits for user input (step 262) and determines when it receives the required user input indicating that the sample preparation of an agricultural product is ready (step 264). This user input may occur in a variety of ways. For example, it may occur through the user selecting the section of a touch screen or entering a particular key stroke in order to initialize the system. When the user initializes the system in the manual mode, or if the system is in an automatic mode, it then executes the same series of steps for sampling and predicting sugar content of a sugar beet or other agricultural products. In particular, it determines when an agricultural product or its sample is present for analysis (step 260), which may accomplished by analysis of the magnitude of the received signal in order to detect a magnitude within a particular range for the agricultural product to be analyzed, or by the use of a separate electronic detector to indicate the presence of a sample.

The electronic detector can be used to both select the agricultural product to be sampled and synchronize the sample preparation mechanism. For example, sugar beets are planted in rows, and the electronic detector can be used to choose a frequency of sampling the sugar beets, such as every third sugar beet in the row. Based on the electronic detector output and the sampling frequency, the operation of the knife or other sample preparation mechanism can be synchronized to prepare a sample of the selected sugar beets. Other types of synchronization can occur through use of such an electronic detector depending upon, for example, the type of agricultural product to be sampled and the harvesting process for that type of agricultural product.

When the system detects that an agricultural product or sample is present (step 266), it performs an analysis of the reflected signal from the agricultural product. In addition, in this example the system also obtains GPS coordinates in order to associate predicted sugar content with a geographical location of the corresponding agricultural product.

When the sample is present, the system obtains GPS coordinates from GPS unit 207 (step 268). It can also or alternatively obtain other indications of a field location of the sampled agricultural product. The field location can be based upon geographical information, such as the GPS coordinates, or upon other information indicating a location of the agricultural product in the field. For example, the user may enter information indicating a field location of the sampled agricultural product, and the entered information can be based upon portions or sectors of the field. The sampled agricultural product can be associated with other types of location information as well such as a harvesting batch, and the harvesting batch can have a correlation with a field location or a grouping of the agricultural products such as, for example, those stored within the same physical bin or storage container.

The system obtains the raw reflected signal from the agricultural product (step 270), as described above, and digitizes the raw reflected signal (step 272) for analysis by computer 36. To perform processing on the digitized signal, the computer can store a particular number of data points within a table, array, or other data structure corresponding with magnitudes of the signal at certain wavelengths between a range $\lambda_k$ to $\lambda_L$. In addition, the computer can store the dark signal, typically determined and stored at the beginning of each operation, for the signal at the corresponding wavelengths. Table 1 illustrates an exemplary array of data points.

TABLE 1

| wavelength | magnitude of received signal | magnitude of dark signal |
|---|---|---|
| $\lambda_k$ | magnitude value 1 | dark signal magnitude value 1 |
| $\lambda_{k+1}$ | magnitude value 2 | dark signal magnitude value 2 |
| ... | | |
| $\lambda_L$ | magnitude value N | dark signal magnitude value N |

An exemplary embodiment for analyzing the sugar content of sugar beets uses 766 data points between wavelengths of 900–1665 nm ($\lambda_{k=900\ nm}$ to $\lambda_{L=1665\ nm}$). Other numbers of data points and ranges of wavelengths may be used as determined through an actual sample measurement, for example, and the type of agricultural product to be analyzed and the particular constituent to be predicted.

Figure 12:
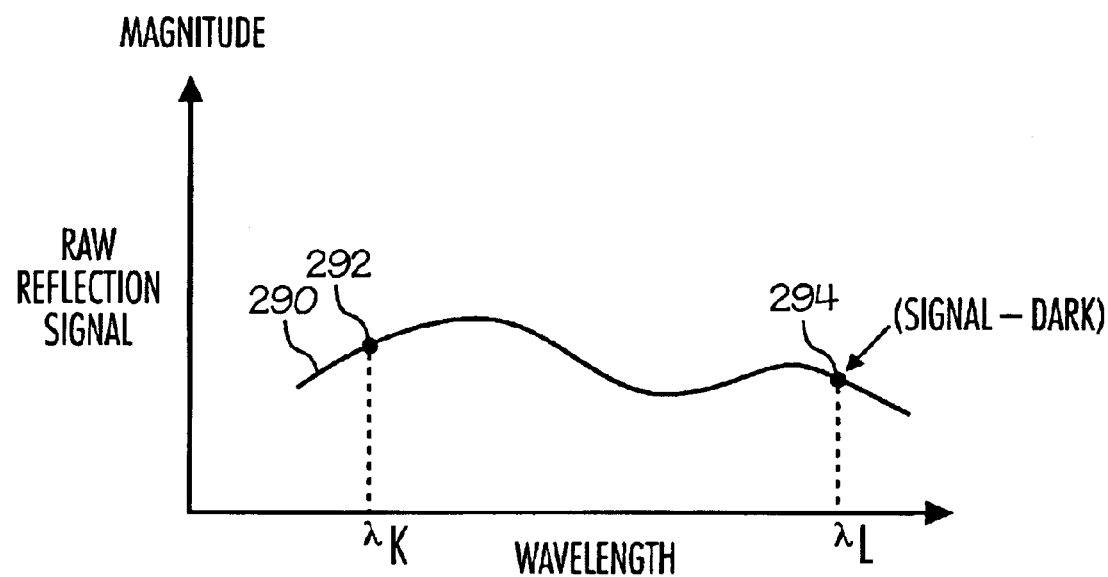
FIG. 12 is a graph of an exemplary raw reflection signal illustrating a portion of the signal to be analyzed between selected wavelengths.

FIG. 12 is a graph illustrating an example of the raw reflection signal 290. Using actual sample measurements, a pair of data points 292 and 294 can be determined corresponding to wavelengths $\lambda_k$ and $\lambda_L$ for determining a relevant portion of the raw reflection signal spectrum for analysis. In an exemplary embodiment for analyzing sugar beets, data point 292 corresponds to a magnitude of the signal at 900 nm and data point 294 corresponds to a magnitude of the signal at 1665 nm.

The computer processes the digitized signal (step 274), which can occur using, for example, two exemplary methods: a reference signal technique, and a reference signal elimination technique. For the reference signal technique, the system pre-processes the digitized signal using the dark signal and normalizes it using the standard reference value using, for example, equation (1) in Table 2. Table 3 provides definitions of the parameters in equation (1).

TABLE 2

Equation (1)

$$[S_{p\lambda}]_{\lambda=k}^{\lambda=L} = \left[\frac{S_{s\lambda} - S_{d\lambda}}{S_{r\lambda} - S_{d\lambda}}\right]_{\lambda=k}^{\lambda=L}$$

TABLE 3

Definitions of parameters for equation (1)

| parameter | definition |
|---|---|
| $S_{p\lambda}$ | processed signal from $\lambda = k$ to $L$ |
| $S_{s\lambda}$ | raw digitized reflected signal (column 2 in Table 1) |
| $S_{d\lambda}$ | dark signal (column 3 in Table 1) |
| $S_{r\lambda}$ | reflected reference signal obtained from a standard reference object or a standard value as identified above |

By using a data structure, the computer can retrieve the values of the data points for each wavelength and compute the processed signal ($S_{p\lambda}$). It can also store the resulting processed signal values in the same table or other data structure, as illustrated by Table 4.

TABLE 4

| wavelength | processed signal ($S_{p\lambda}$) |
|---|---|
| $\lambda_k$ | value 1 |
| $\lambda_{k+1}$ | value 2 |
| ... | |
| $\lambda_L$ | value N |

The computer then computes the logarithm of the pre-processed signal using, for example, equation (2) in Table 5.

TABLE 5

Equation (2)

$$S_{L\lambda} = \log_{10}(S_{p\lambda})_{\lambda=k}^{\lambda=L}$$

Alternatively, the computer can process the digitized signal (step 274) using the reference signal elimination technique, which does not involve use of the standard reflectance value obtained in step 254. For the reference signal elimination technique, the system subtracts the dark signal from the raw spectra signal using, for example, equation (3) in Table 6.

TABLE 6

Equation (3)

$$S_{u\lambda} = (S_{s\lambda} - S_{d\lambda}), \text{ for } \lambda = k \text{ to } L$$

The parameters $S_{s\lambda}$ and $S_{d\lambda}$ in equation (3) have the same definitions as provided in Table 3. The computer then calculates a value to normalize the data; in this exemplary embodiment, it calculates the value using equation (4) in Table 7 to determine the average value for the data points $S_{u\lambda}$.

TABLE 7

Equation (4)

$$S_{\lambda d} = \frac{\sum [S_{u\lambda}]_{\lambda=k1}^{\lambda=L1}}{N}$$

In an exemplary embodiment for analyzing the sugar content of sugar beets, k1=1150 nm and L1=1200 nm in equation (4).

As a first alternative to equation (4) in Table 8, the computer can use equation (5) to calculate the value used to normalize the data as any mathematical function relating to magnitudes of the signal at one or more selected wavelengths.

TABLE 8

Equation (5)

$$S_{\lambda d} = Q = f(\lambda_1, \lambda_2, \lambda_3, \ldots, \lambda_n, \text{ or } \lambda_r)$$

where f = any mathematical function

As a second alternative to equation (4), the computer can use equation (6) in Table 9 to calculate the value used to normalize the data.

TABLE 9

Equation (6)

$$S_{\lambda_d} = S_{\lambda_b} = f([S_\lambda]_{\lambda=q}^{\lambda=t})$$

where $S_\lambda$ = signal at a given wavelength, $\mu$, and
f = any linear and/or non-linear function that may or may not be dependent of $\mu$.

Using equation (7) in Table 10, for example, the computer normalizes the data points $S_{u\lambda}$, using the average value from equation (4), or the values from equations (5) or (6), or another normalizing value. Table 11 provides definitions of parameters in equation (7).

TABLE 10

Equation (7)

$$S_{n\lambda} = \left[\frac{S_{u\lambda}}{S_{\lambda d}}\right]_{\lambda=k}^{\lambda=L}$$

TABLE 11

Definitions of parameters for equation (7)

| parameter | definition |
|---|---|
| $S_{n\lambda}$ | normalized signal from $\lambda = k$ to $L$ |
| $\lambda_d$ | normalizing wavelength, $\lambda_d = \lambda_1$, or $\lambda_2$ or $\lambda_3 \ldots, \lambda_n$, or $\lambda_r$ |
| $\lambda_1$, or $\lambda_2$ or $\lambda_3 \ldots, \lambda_n$ | wavelength with highest or higher or same correlation as the concentration of the constituent |
| $\lambda_r$ | reference wavelength or equivalent of a band of wavelengths that does not contribute to the concentration of the desired constituent or does not have any substantial correlations with the concentration of the desired constituent |

The reference wavelength $\lambda_r$ could be predetermined from prior experiments, or through an actual sample measurement. For example, through testing it can be determined that a particular wavelength does not have any substantial correlation with the desired constituent. In other words, the value of the constituent does not substantially affect the intensity of the reflected signal at that wavelength. In order to account for minor variations in the intensity at the reference wavelength based on other factors apart from constituent content, the system may use an average magnitude value of a band of wavelengths centered around the reference wavelength to normalize the spectral signal. For the band of wavelengths, the system can process the signal magnitude using any suitable mathematical function. One such example is to use a summation of the intensities at selected wavelengths centered around the reference wavelength and divide the summation by the total number of wavelengths. The use of this type of reference wavelength or band of wavelengths is further described in the related application for optical analysis of a stream of an agricultural product, as identified above.

The computer then calculates the logarithm of the normalized data points using, for example, equation (8) in Table 12.

TABLE 12

Equation (8)

$$S_{L\lambda} = \log_{10}(S_{n\lambda})_{\lambda=k}^{\lambda=L}$$

Table 13 provides a summary of the equations and corresponding sub-steps for implementing step 274 using the exemplary reference signal technique and reference signal elimination technique.

TABLE 13

| equation | sub-step |
|---|---|
| | Reference Signal Technique |
| (1) | pre-process the raw reflected signal to subtract the dark signal from the raw spectra signal and to normalize the data points using the reference signal |
| (2) | calculate the logarithm of the normalized data points to linearize the data |
| | Reference Signal Elimination Technique |
| (3) | subtract the dark signal from the raw spectra signal |
| (4), (5), or (6) | calculate a value for use in normalizing the data points |
| (7) | normalize the data points using the calculated value |

TABLE 13-continued

| equation | sub-step |
|---|---|
| (8) | calculate the logarithm of the normalized data points to linearize the data |

For both techniques the computer reduces the normalized signal ($S_{L\lambda}$), meaning the data points resulting from equations (2) or (8), using an averaging technique (step 276). In an exemplary embodiment, it used a six-to-one averaging technique by computing averages of groups of six adjacent data points to reduce the number of data points by a factor of six. Any type of averaging can be used to reduce the number of data points as necessary or desired for subsequent processing.

The reduced signal is then processed using a prediction technique to determine the sugar content (step 278). A variety of techniques are known in the art for obtaining an indication of sugar content once the normalized (and possibly reduced) signal has been determined. Calculating the logarithm of the data points in equations (2) and (8) is performed to further process/linearize the data for using the standard techniques.

The set of linearized data points $S_L$ can then be processed according to standard techniques for the particular constituent desired and type of agricultural product sampled. These standard techniques can involve statistical analysis of the data points, which can be accomplished using conventional software for performing the particular statistical analysis functions on the data.

As an example, the $S_L$ data points were tested and processed as follows for determining the sugar content of a sugar beet. Using GRAMS-32, version 5.03, a software program from Galactic Industries, N.H., the signal $S_L$ was further processed as follows: offset correction was performed on the y-axis with the option of "set point to zero"; the signal was smoothed using "binomial smoothing" with the number of points equal to four; the data was reduced by a factor of six-to-one using an averaging technique under the interpolation option of the software, used to perform step 276; and a second derivative was calculated with a gap value equal to 18.

After the processing of $S_L$, 121 data points represented the spectral signal of the sugar beet sample. The processing used a 490×121 training data set and a 127×121 test data set.

The data were then further processed using Principle Component Regression (PCR) and Partial Least Square (PLS) to develop a prediction model, using SAS software from Statistical Analysis Software, N.C. The prediction model predicted the sugar content percentage for the sugar beet sample. Examples of statistical and neural network models for predicting the sugar content of citrus fruits are provided in the following texts, which are incorporated herein by reference: Suming Chen, Kuang-Wen Hsieh, and Wen-Hung Chang, "Neural Network Analysis of Sugar Content in Fruit Juice," Paper No. 993083 presented at the 1999 ASAE/CSAE-SCGR Annual International Meeting, Jul. 18–21, 1999; and Renfu Lu, Daniel Guyer, and Randolph Beaudry, "Determination of Sugar Content and Firmness of Apples Using Near-Infrared Diffuse Reflectance," Paper No. 006120 presented at the 2000 ASAE Annual International Meeting, Jul. 9–12, 2000.

The following is an example of other components used for testing of the embodiment to predict sugar content of sugar beets. Spectrometer 211 was implemented with a PC-based fiber optic coupled spectrometer from Control Development, Inc., IN. The white reflectance standard from Lab Sphere (NH) was used for the value $S_{rλ}$, in equation (1). The particular wavelength range and number of data points used are identified above. Fiber optic cable 37 was implemented with an IR-VIS multi-mode optical fiber from OZ Optics, Ltd., Ontario, Canada. The light or illumination source used a gold coated illumination lamp, 75W, from Gilway, Mass.

To check the accuracy of the testing, a $C^{++}$ program, using Microsoft Visual $C^{++}$, was developed to compare the predicted sugar content with the original or actual sugar content and provide an accuracy percentage, standard deviation, and other such statistical measurements of accuracy. The original or actual sugar content of the sugar beet was determined using standard laboratory techniques for determining sugar content.

This testing illustrates only one example of processing the data points, and other conventional techniques and software programs can be used.

Once it obtains the indication of sugar content, the system stores the GPS coordinates and corresponding indication of sugar content (step 280). This information can be stored within a database structure such as a table or relational database for subsequent processing and display, such as is shown in Table 14. The system can also store other location information corresponding with the sugar content indication such as a field location or a harvesting batch, both of which are explained above. The field location or harvesting batch information can be stored, for example, in a table similar to that shown in Table 14 with the field location or harvesting batch information substituted for or included in addition to the GPS coordinates.

TABLE 14

| GPS coordinates | | |
|---|---|---|
| longitude | latitude | sugar content |
| longitude value 1 | latitude value 1 | sugar content value 1 |
| longitude value 2 | latitude value 2 | sugar content value 2 |
| ... | | |
| longitude value N | latitude value N | sugar content value N |

The system can also display the GPS coordinates and indication of corresponding sugar content in order to provide a real-time or near real-time indication of sugar content during, for example, the harvesting process (282). If the system is in automatic mode (step 284), the system returns to step 260 to wait for detection of another agricultural product or sample present for analysis. Otherwise, if the system is in the manual mode it returns to step 262 in order to wait for user input in order to trigger detection and analysis of another agricultural product or sample.

FIG. 13 is a diagram of a screen 300 for displaying the GPS coordinates and indication of corresponding sugar content as part of step 282. Screen 300 includes a first section 302 for displaying and indication of sugar content such as a numerical indication of a sugar percentage. It also includes sections 304 and 306 for providing an indication of corresponding longitude and latitude coordinates of the agricultural product having the sugar content displayed in section 302. Therefore, when harvesting sugar beets, for example, the system can display to a user a real-time or near real-time indication of sugar content during the harvesting of various parts of a field.

Figure 14:
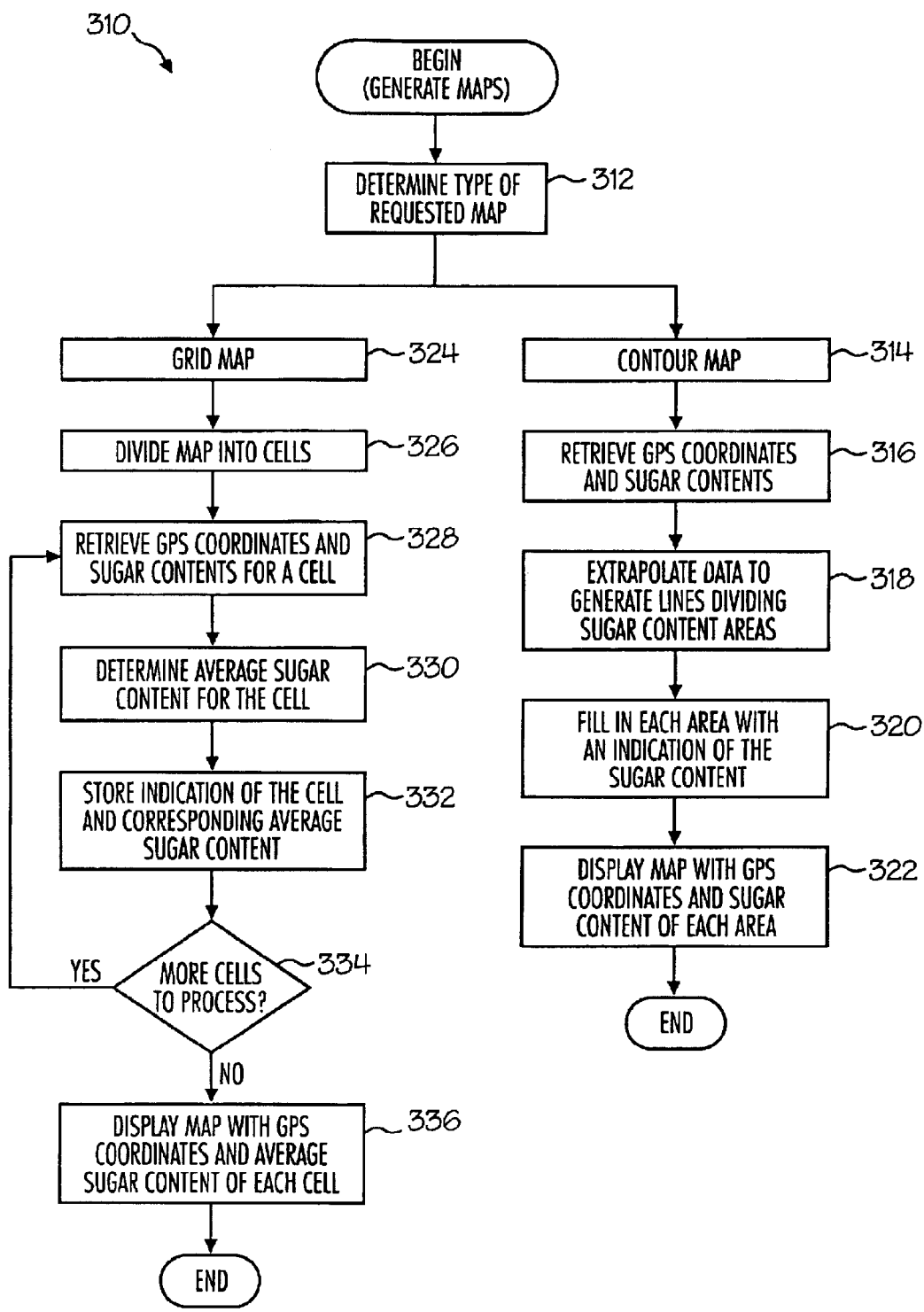
FIG. 14 is a flow chart of a generate map routine for use in generating an indication of sugar content across a field of harvested agricultural products.

FIG. 14 is a flow chart of a generate map routine 310 triggered by step 232 in main routine 220. Routine 310 can be used to generate and display a grid map and a contour map providing an indication of sugar content across a field of an agricultural product. FIG. 15 is a diagram of an exemplary grid map 340, and FIG. 16 is a diagram of an exemplary contour map 350. Grid map 340 divides the field into a plurality of cells and displays a first axis 342 having longitude coordinates and a second axis 344 having latitude coordinates. A plurality of cells, such as cell 346, provide an indication of an average sugar content for that portion of the field. Any number of cells may be used depending on the requirements of a particular application.

Contour map 350 also provides an indication of sugar content among a field but instead of using cells it uses lines for dividing areas of different sugar contents. It includes a first axis 352 providing longitude coordinates and a second axis 354 providing latitude coordinates. Various sections, such as section 356 provide an indication of sugar content for the corresponding area of the field. Contour map 350 can also include a corresponding key 358 indicating which visual depictions correspond to which particular indications of sugar content. Various types of visual indications may be used in addition to the one shown. For example, the system may use different colors or shading for indicating different indications of sugar content.

In routine 310, the system determines which map was requested by the user (step 312). If the user selected the contour map (step 314), the system retrieves the GPS coordinates and corresponding sugar contents from the database, such as from Table 14 (step 316). The system extrapolates the data to generate lines dividing the sugar content areas (step 318). Any number of extrapolation techniques may be used. The system fills in each area with an indication of the sugar content (step 320) and displays a map with the GPS coordinates and sugar content of each area (step 322), an example of which is shown as contour map 350.

If the user has selected the grid map (step 324), the system divides the map into a plurality of cells (step 326). The system retrieves the GPS coordinates and sugar contents for a particular cell (step 328), and determines the average sugar content for the cell (330). The average sugar content may be determined by adding all the sugar content values for the cell and dividing by the total number. The system stores an indication of the cell and corresponding average sugar content (step 332), and determines if more cells exist to process (step 334). If there are more cells to process, the system repeats steps 328, 330, and 332 to determine the average sugar content for the next cell. Upon processing all cells, the system displays a map with GPS coordinates and average sugar content of each cell (step 336), an example of which is shown as grid map 340.

The system can also store the generated grid and contour maps in order to avoid having to repeatedly generate them. These maps may be displayed in a variety of ways. They may be displayed on a display device or printed out in hard copy form.

These maps may also be used to display sugar content for a wide variety of agricultural products. They may be used to display sugar content for a field containing sugar beets as gathered by the optical sensor on harvester as explained above. In addition, they may be used to provide a map of sugar content of grapes throughout the field of a winery. In that example, the optical sensor and associated computer may be contained within a hand-held or other type of portable unit and be used to sample grapes in a variety of locations. Upon sampling each grape, the system can store the corresponding GPS coordinates or user-entered location information. Therefore, the system can use the same routines 250 and 310 for generating a map of the sugar content among the grapes in the field of a winery. This information may be useful for the winery in determining the type and quality of wine it produces. The same technique could be used for the fields or orchards of various citrus fruits, such as grapefruits or oranges.

The algorithm and processing hardware described above are selected and optimized so that the spectral analysis results can be developed in seconds or fractions of a second. This permits on-the-go, near real-time, or user-defined frequent sampling of the agricultural product, so that as a harvester/defoliator moves, multiple data points representing sugar content at closely spaced points in a field can be generated. In particular, the average spacing between sugar beet roots during harvesting is twelve inches, and the spacing between each row is approximately thirty inches.

The optical sensor configuration described in this specification for analyzing sugar beets has been shown for one row only in FIG. 2 for illustrative purposes. The sensor could be mounted for multiple rows on a defoliator for simultaneously sampling and measuring sugar content of sugar beets in multiple rows during harvesting. All of the data from that sampling could be input and stored on a single computer. This sampling may generate a map of the sugar content, and hence an indication of quality, of agricultural products throughout the field.

Alternate Embodiment: Portable Optical Sensor

In addition to on-the-go sensing, agricultural products can be optically analyzed in a static mode using, for example, a portable optical sensor. For certain implementations, the agricultural products need not necessarily be analyzed during harvesting. Once harvested, the agricultural products can be analyzed using the portable optical sensor. For certain agricultural products, such as grapes, they can be analyzed without harvesting and while still on the grapevine. The portable optical sensor also permits analysis directly in the field of selected agricultural products such as citrus fruits. For example, the portable optical sensor can be carried or otherwise transported throughout an orchard for analysis of selected citrus fruits at various locations. As an alternative to a portable unit, the static mode can involve analysis of agricultural products brought to a unit that is not necessarily portable, such as analyzing the agricultural products in a food processing plant.

Figure 17:
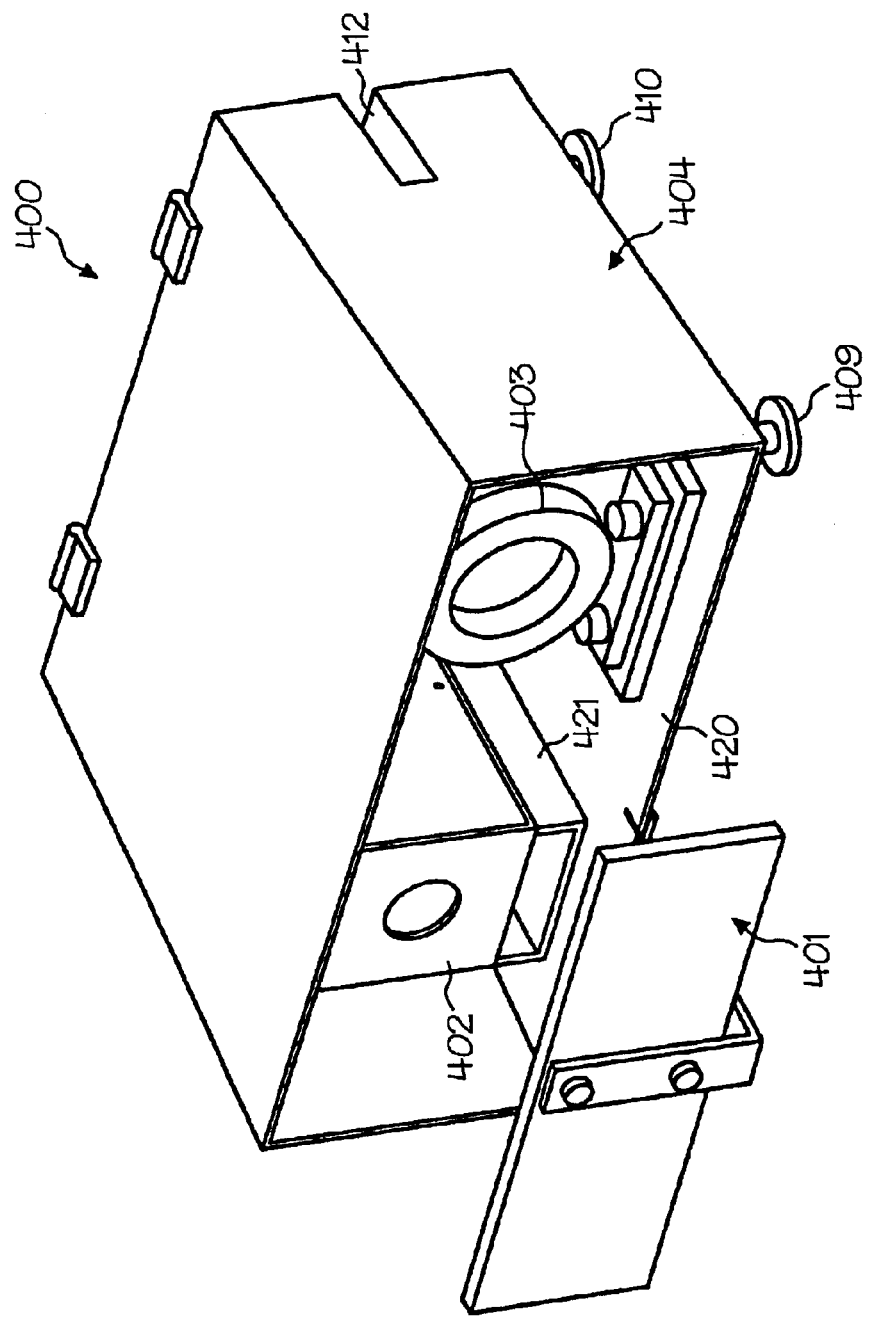
FIG. 17 is a perspective view of a portable version of the optical sensor.
Figure 18B:
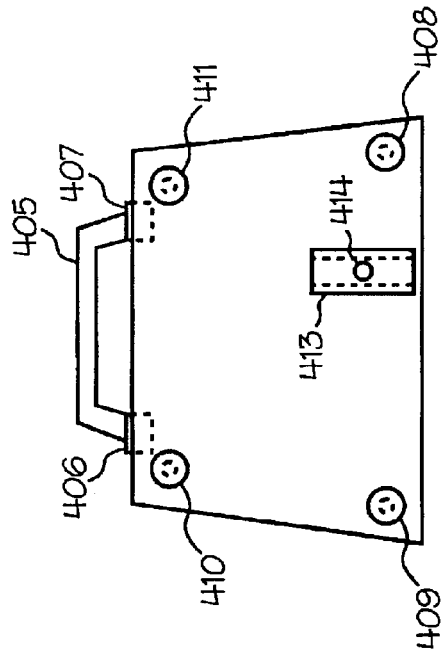
FIGS. 18A–18D are top, bottom, back, and side views of the portable optical sensor shown in FIG. 17.
Figure 18D:
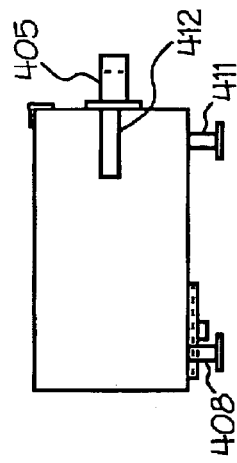
Figure 18A:
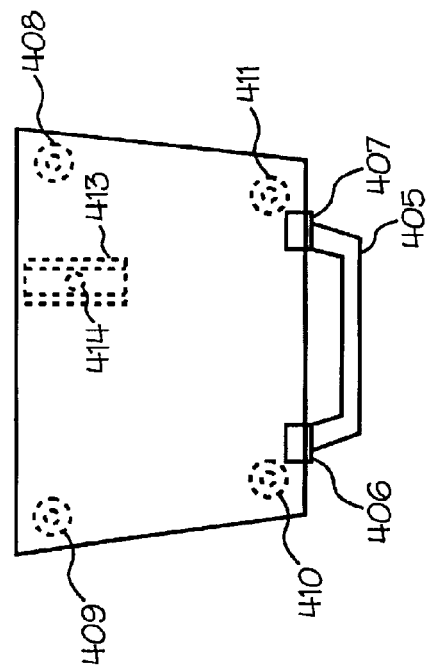
Figure 18C:
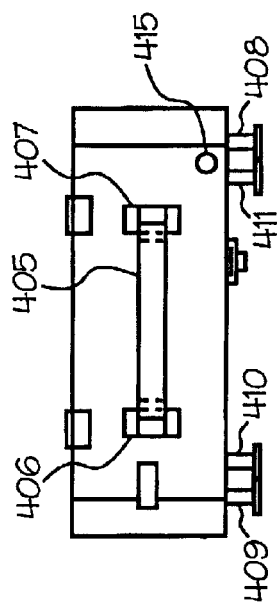
Figure 19B:
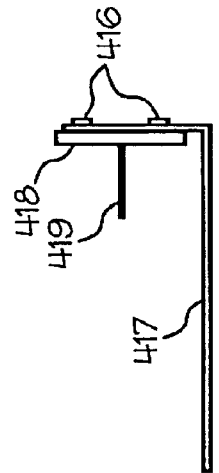
FIGS. 19A–19D are perspective, side, front, and bottom views of a sample holder for the portable optical sensor shown in FIG. 17.
Figure 19D:
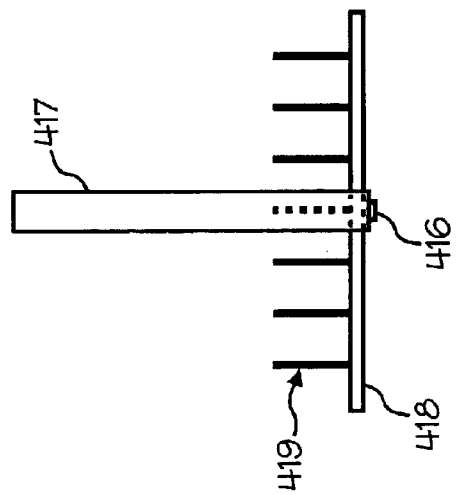
Figure 19A:
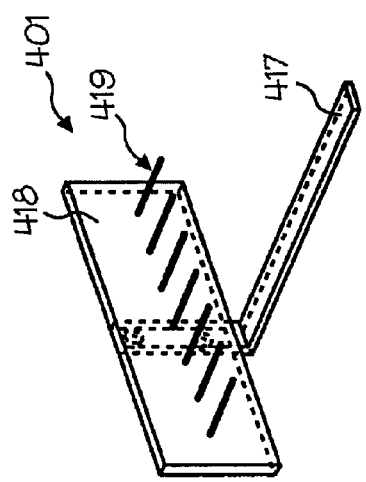
Figure 19C:
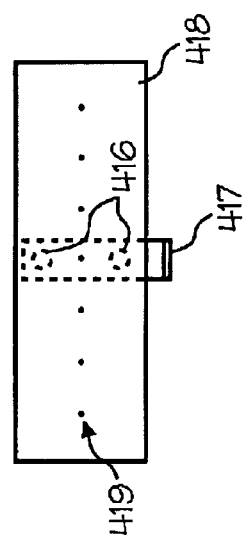

FIG. 17 is a perspective view of a portable version 400 of the optical sensor. Portable optical sensor 400 includes a housing 404 containing both an illumination chamber 402 and a sensor head 403, which can be implemented with the same components as illumination chamber 38 and sensor head 39 described above. Illumination chamber 402 and a sensor head 403 are mounted on a base platform 420, and illumination chamber 402 includes a light box stand bracket 421 for mounting it on the platform 420. Housing 404 can be implemented with, for example, a metal or other opaque material for blocking ambient light and providing sufficient structural support for illumination chamber 402 and sensor head 403.

A sample holder 401 can hold in position an agricultural product or a sample of it in order for it to be radiated for optical analysis. Housing 404 contains an open end for allowing illumination chamber 402 to radiate a sample of an agricultural product held on sample holder 401, facing the open end, and for allowing sensor head 403 to receive reflected radiation from the sample. As an alternative to the open end, housing 404 can contain a plate over the open end with apertures for passing the transmitted and reflected radiation.

Portable sensor 400 includes four legs, of which legs 409 and 410 are shown in FIG. 17, for resting on a substantially flat surface during the analysis of the agricultural product. A fiber optic cable slot 412 can accommodate a fiber optic cable for transmitting a received light signal to a spectrometer and computer, such as computer 36, for processing. Computer 36 can be implemented with a portable computer, such as a laptop or notebook computer, for transporting with portable optical sensor 400. Computer 36 can execute the same methods explained above with reference to the flow charts in FIGS. 8, 10, 11, and 14.

FIGS. 18A, 18B, 18C, and 18D are, respectively, top, bottom, back, and side views of portable optical sensor 400. As illustrated in FIGS. 18A–18D, portable optical sensor 400 includes legs 408, 409, 410, and 411 for resting on a surface during the analysis. A handle 405 can be attached to housing 404 using hinges 406 and 407 for carrying the portable optical sensor 400. An adjustable sliding holder 413 accommodates sample holder 401, and includes a bolt for fixing sample holding 401 in position among variable positions. As shown in the back view in FIG. 18C, the portable optical sensor 400 can include a hole 415 for wiring to illumination chamber 402 and sensor head 403.

FIGS. 19A, 19B, 19C, and 19D are, respectively, perspective, side, front, and bottom views of sample holder 401 for portable optical sensor 400. The term "sample holder" includes any device for holding in place a sample of an agricultural product to be radiated, and this illustrated sample holder is only one such example. Sample holder 401 holds in place an agricultural product, or a portion of it, for receiving a light signal from illumination chamber 402 and reflecting a signal to sensor head 403. Sample holder 401 has an adjustable arm 417 for placement within sliding holder 413 and secured into position by tightening bolt 414 against it. Sample holder 401 also has a sample supporting plate 418 attached to movable arm 417 through fasteners 416 such as bolts. Plate 418 includes several anchoring pins 419 for holding a sample of the agricultural product against it. The anchoring pins 419 are preferably of a length such that when a sample is mounted on plate 418 the pins do not completely pierce or show through on the surface of the sample to be radiated. However, they firmly hold the sample. As an alternative to pins, other anchoring mechanisms can be used, and the term "anchoring mechanism" includes any type of element or structure for firmly holding the sample in place.

The components of sample holder 401 can be implemented with, for example, the following: iron or metal for arm 417, wood for plate 418, and nails for anchoring pins 419. The wood for plate 418 is preferably painted black or other such color to minimize reflections of the light signal and provide a low reflectance from surrounding areas on a surface of plate 418 not covered by the agricultural product sample.

Figure 20A:
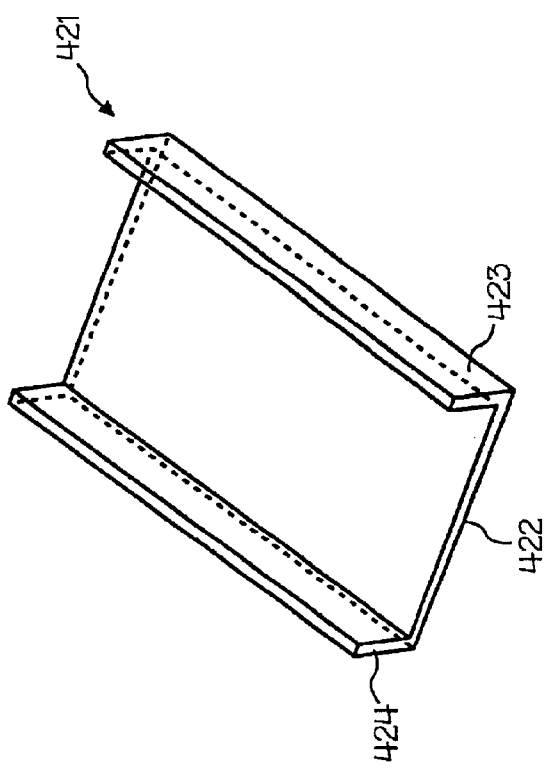
FIGS. 20A–20C are perspective, side, and front views of a light box stand bracket for the portable optical sensor shown in FIG. 17.
Figure 20C:
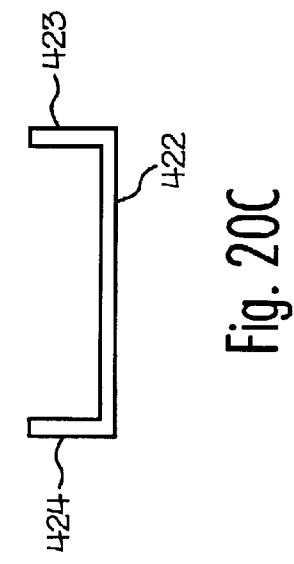
Figure 20B:
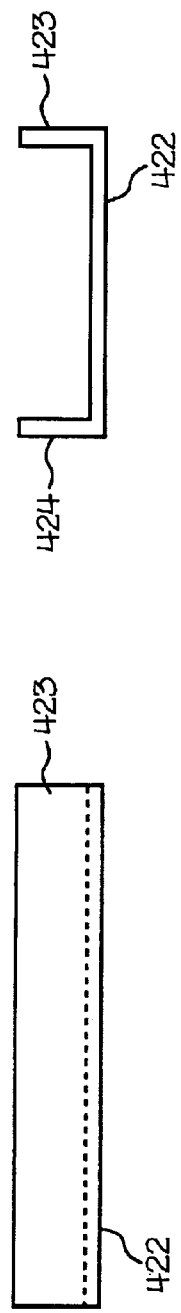

FIGS. 20A, 20B, and 20C are, respectively, perspective, side, and front views of light box stand bracket 421 for mounting illumination chamber 403. Bracket 421 includes a bottom 422 for attachment against platform 420 using, for example, welding, fasteners, or adhesive. Bracket 421 also includes sides 423 and 424 on which is mounted illumination chamber 403.

FIGS. 18A–18D, 19A–19D, and 20A–20C provide dimensions in inches of an exemplary embodiment for portable optical sensor 400. Other portable optical sensors can have different dimensions and configurations, and otherwise use the same techniques to radiate and process radiation reflected from or transmitted through an agricultural product or a sample of it.

Figure 21:
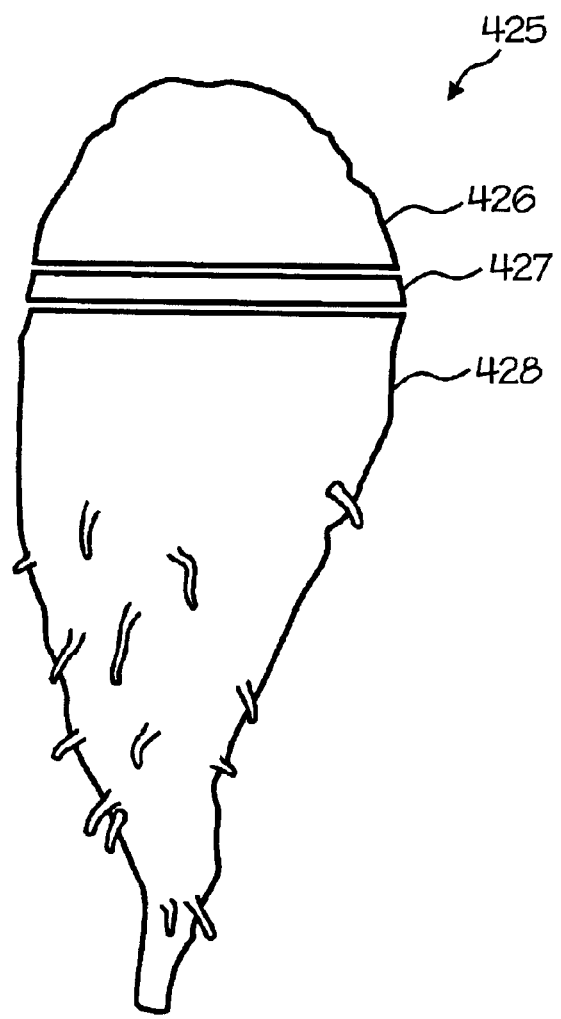
FIG. 21 is a diagram illustrating a procedure for obtaining a sample of a sugar beet for analysis by the portable optical sensor.

FIG. 21 is a diagram illustrating a procedure for obtaining a sample of a sugar beet for analysis by portable optical sensor 400. For a sugar beet 425, a small section 426 from the top of the beet is cut out with a knife or other cutting instrument. Another thin cross section 427 of the beet is cut out from the remainder 428 of the beet. The sample 427 is mounted on anchoring pins 419 of sample holder 401. Using adjustable arm 417 mounted in sliding holder 413, the appropriate distance is set between the sample surface and the illumination chamber 402.

Figure 22:
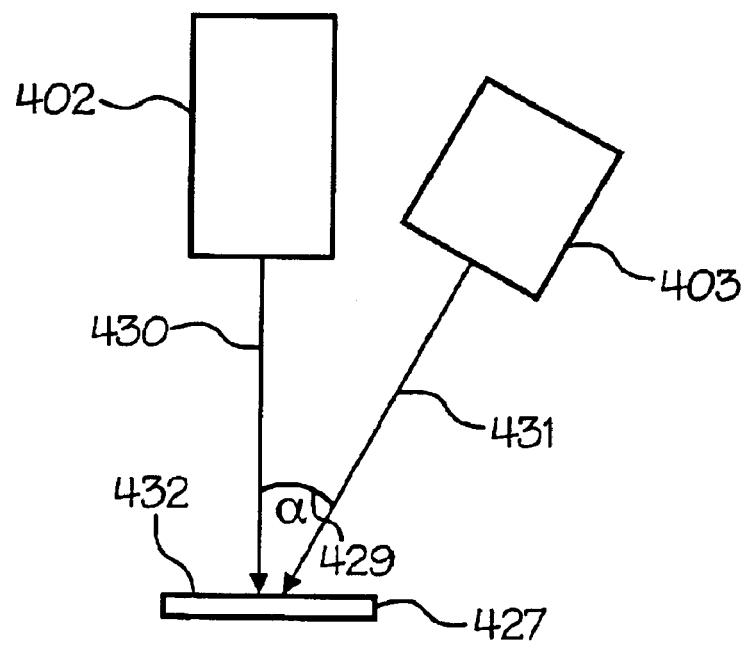
FIG. 22 is a diagram illustrating distance and angle parameters between a light box, sensor head, and sample for analyzing a sample using the portable optical sensor.

FIG. 22 is a diagram illustrating exemplary distances 430 and 431, and an angle 429, between illumination chamber 402, sensor head 403, and sample 427 for analyzing the sample using the portable optical sensor 400. Experiments or actual sample measurements can be used to determine the optimum angle α (429), distance $L_1$ (430) between illumination chamber 402 and a surface 432 of sample 427, and the distance $S_1$ (431) between sensor head 403 and sample surface 432. The sample is placed on sample holder 401, which is then positioned by moving adjustable arm 417 in sliding holder 413 so that the required distance requirements are met. When the light signal from illumination chamber 402 falls on the sample surface 432, the reflected NIR spectrum is obtained by the sensor head 403, and the spectral signature can be acquired and processed to predict sugar content or other constituent using the methods described above.

In testing an exemplary embodiment for predicting sugar content of a sugar beet slice, the following distance and angle parameters were used: distance $S_1$=15.7 centimeters (cm) (431); distance $L_1$=10 centimeters (430); and angle α=40° (429). These are exemplary parameters only for one particular embodiment. Optimum distance and angle parameters depend upon, for example, the type of agricultural product to be sampled and the particular constituent to be predicted, and those parameters can be determined through actual sample measurements or in other ways.

Although embodiments have described with reference to predicting the sugar content of a sugar beet, the apparatus and methods described above can be used with many types of agricultural products for predicting various types of constituents. For example, it can be used for predicting the sugar content or other constituent of grapes, grapefruits, oranges, or other fruits. The constituents can be predicted on-the-go or in near real-time during harvesting or in a static mode either in the field or at a separate location. For certain fruits, such as grapes, that have a translucent outer covering the methods and apparatus can be used to predict the sugar content in a non-invasive way, which provides the advantage of predicting sugar content without destruction of the fruit.

While the present invention has been described in connection with an exemplary embodiment, it will be understood that many modifications will be readily apparent to those skilled in the art, and this application is intended to cover any adaptations or variations thereof. For example, different types of materials for the device, and various types of software algorithms for processing the signal resulting from irradiation of the agricultural product, may be used without departing from the scope of the invention. This invention should be limited only by the claims and equivalents thereof.

What is claimed is:

1. A method for processing a spectral signal to predict sugar content of an agricultural product, comprising;
    receiving a light signal from an agricultural product;
    converting the light signal into a spectral signal;
    digitizing the spectral signal to produce a plurality of data points; and
    processing the data points using dark signal values and a reference signal value to produce a plurality of normalized data points, the normalized data points having values related to sugar content of the agricultural product, and wherein the reference signal value is related to a magnitude at one or more wavelengths of the spectral signal,
    wherein the processing step includes using as the reference signal value average magnitude value of a range of magnitude values within a pair of wavelengths centered around a reference wavelength.

2. The method of claim 1 wherein the receiving step includes receiving the light signal reflected from the agricultural product.

3. The method of claim 1, further including reducing the plurality of normalized data points.

4. The method of claim 1, further including predicting sugar content of the agricultural product using the plurality of normalized data points.

5. A method for processing a spectral signal to predict sugar content of an agricultural product, comprising:
    receiving a light signal from an agricultural product;
    converting the light signal into a spectral signal;
    digitizing the spectral signal to produce a plurality of data points;
    processing the data points using dark signal values and a reference signal value to produce a plurality of normalized data points, the normalized data points having values related to sugar content of the agricultural product, and wherein the reference signal value is related to a magnitude at one or more wavelengths of the spectral signal;
    predicting sugar content of the agricultural product using the plurality of normalized data points;
    receiving geographical coordinates corresponding with a geographical location of the agricultural product; and
    associating the geographical coordinates with the predicted sugar location of the agricultural product.

6. A method for processing a spectral signal to predict sugar content of an agricultural product, comprising:
    receiving a light signal from an agricultural product;
    converting the light signal into a spectral signal;
    digitizing the spectral signal to produce a plurality of data points;
    processing the data points using dark signal values and a reference signal value to produce a plurality of normalized data points, the normalize data points having values related to a magnitude at one or more wavelengths of the spectral signal;
    receiving a plurality of geographical coordinates corresponding with geographical locations of a plurality of agricultural products for which sugar contents are predicted using the method; and
    associating the plurality of geographical coordinates with the predicted sugar contents of the plurality of agricultural products.

7. The method of claim 6, further including generating a map of the sugar contents of the agricultural products using the plurality of geographical coordinates and the associated predicted sugar contents.

8. The method of claim 7, wherein the generating step includes generating a grid map.

9. The method of claim 7, wherein the generating step includes generating a contour map.

10. A method for processing a spectral signal to predict sugar content of an agricultural product, comprising:
   receiving a light signal from an agricultural product;
   converting the light signal into a spectral signal;
   digitizing the spectral signal to produce a plurality of data points; and
   processing the data points using dark signal values and a reference signal value, eliminating the use of a spectral signature of a separate physical standard, to produce a plurality of normalized data points, the normalized data points having values related to sugar content of the agricultural product, wherein the processing step includes using as the reference signal value an average magnitude value of a range of magnitude values within a pair of wavelengths centered around a reference wavelength.

* * * * *